United States Patent [19]

Van Rheenen

[11] Patent Number: 4,548,748
[45] Date of Patent: Oct. 22, 1985

[54] CYANOHYDRIN PROCESS

[75] Inventor: Verlan H. Van Rheenen, Portage, Mich.

[73] Assignee: The Upjohn Company, Kalamazoo, Mich.

[21] Appl. No.: 576,674

[22] Filed: Feb. 3, 1984

[51] Int. Cl.$^4$ .............................................. C07J 5/00
[52] U.S. Cl. .................... 260/239.55 C; 260/397.45; 260/397.5
[58] Field of Search ................. 260/397.45, 239.55 C, 260/397.5

[56] References Cited

U.S. PATENT DOCUMENTS

| | | | |
|---|---|---|---|
| 3,496,169 | 2/1970 | Nagata | 260/239.55 |
| 4,041,055 | 8/1977 | Shephard et al. | 260/397.3 |
| 4,216,159 | 8/1980 | Hessler et al. | 260/397.1 |
| 4,342,702 | 8/1982 | Walker | 260/397.3 |
| 4,348,327 | 9/1982 | Nickolson et al. | 260/397.1 |

FOREIGN PATENT DOCUMENTS

| | | | |
|---|---|---|---|
| 147669 | 4/1981 | German Dem. Rep. | 260/397.4 |
| 7062296 | 4/1982 | Japan | 260/397.45 |
| 7062297 | 4/1982 | Japan | 260/397.45 |
| 7062298 | 4/1982 | Japan | 260/397.45 |
| 7062299 | 4/1982 | Japan | 260/397.45 |
| 7062300 | 4/1982 | Japan | 260/397.45 |
| 2086907 | 5/1982 | United Kingdom | 260/397.3 |

OTHER PUBLICATIONS

*Steroids,* 28, (1976) pp. 89-99, H. Kuhl et al.
*Helv. Chim. Acta,* 21 (1938) pp. 1317-1326, K. Miescher et al.$n 30 *J. Am. Chem. Soc.,* 75, (1953), pp. 650-653, A. Ercoli et al.
*Helv. Chem. Acta,* 29 (1946), pp. 1580-1586, K. Meyer.
*J. C. S. Perkin* I (1975) pp. 1242-1244, R. B. Boar et al.
*J. C. S. Chem. Comm.* (1981) pp. 774-775, D. H. R. Barton et al.
*Steroids,* 37 (1981), pp. 361-382, A. Belanger et al.
*J. Am. Chem. Soc.,* 81 (1959) pp. 5725 $\propto$ 5727, P. Ruggieri et al.
*Tetrahedron Letters,* 22, (1971) pp. 2005-2008, J. C. Gasc et al.
*Helv. Chem. Acta,* 33 (1950), pp. 1093-1105, H. Heusser et al.

*Primary Examiner*—Elbert L. Roberts
*Attorney, Agent, or Firm*—Bruce Stein

[57] ABSTRACT

Using cyanohydrin intermediates, 17-keto steroids are transformed to corticoids and 17α-acyl progesterones.

18 Claims, No Drawings

CYANOHYDRIN PROCESS

BACKGROUND OF THE INVENTION

There are a number of chemical processes for transformation of 17-keto steroids to the corresponding 17α-hydroxypregna steroids, see U.S. Pat. No. 4,041,055 and Tetrahedron Letters 22, 2005 (1971). Likewise, chemical processes are known for the transformation of 17-keto steriods to the corresponding corticoids, see U.S. Pat. Nos. 4,041,055, 4,342,702, 4,216,159, and Great Britain Pat. No. 2,086,907A.

The literature also sets forth processes for the transformation of the 17β-cyano-17α-hydroxy steroid (I) to the corresponding 17α-acyloxyprogesterone (VI) see P. deRuggieri, et al., J. Am. Chem. Soc. 81, 5725 (1959); J. C. Gasc, et al., Tetrahedron Letters 22, 2005 (1971); A. Belanger, Steroids 37, 361 (1981); and Japanese Pat. Nos. J5 7,062,296, J5 7,062,297, J5 7,062,299 and J5 7,062,300.

17β-Cyano-17α-hydroxy steroids (I) have been produced from the corresponding 17-keto steroids, see A. Ercoli, et al., J. Am. Chem. Soc. 75, 650 (1953); H. Heusser, et al., Helv. Chem. Acta 33, 1093 (1950); K. Meyer, Helv. Chim. Acta 29, 1580 (1946); K. Miescher, et al., Helv. Chim. Acta 21, 1317 (1938); H. Kuhl, et al., Steroids 28, 89 (1976), U.S. Pat. No. 3,496,169 and East German Pat. No. 147,669. Japanese Pat. Nos. J5 7,062,296, J5 7,062,299 and J5 7,062,300 also include 17β-cyano-17α-hydroxyandrost-4,9(11)-dienes (IA). J. C. Gasc, et al., Tetrahedron Letters 22, 2005 (1971) reported the preparation of 19-nor-17β-cyano-17α-hydroxyandrost-5(10),9(11)-dienes.

17β-Cyano-17α-hydroxy steroids (I) are known where the 17α-hydroxy group is protected as an ester. See, for example, Helv. Chem. Acta 29, 1580 (1946) formula IV on p. 1582 and Helv. Chem. Acta 33, 1093 (1950) formula XIII on p. 1096. These compounds are also known where the 17α-hydroxy group is protected as an ether (II). See, for example, Steroids 37, 362 (1981) on p. 362 the TMS ether; J. Am. Chem. Soc. 81, 5725 (1959) on p. 5726 formula III as the THP ether; Tetra. Lett. 22, 2005 (1971) on p. 2007 formula IX as the TMS ether; and Japanese Pat. No. 7,062,296 for the butyl vinyl ether. U.S. Pat. No. 4,348,327 discloses 17β-cyano-17α-hydroxy steroids of the $\Delta^4$-3-keto (A) and 3β-hydroxy-$\Delta^5$ (C) type which may or may not have methyl substitution at $C_{16}$ but which have no substitution in the C ring.

D. H. R. Barton, et al., J.C.S. Chem. Comm. 774 (1981) reported producing a 3β-O-substituted-$\Delta^5$-enimide similar to the enimide (III) where the protecting group at 17α was acetate and the substituent on the enimide nitrogen at $C_{20}$ was —CHO. It should be noted that Barton, et al. did not produce his 3β-O-substituted-$\Delta^5$-enimide from a 17β-cyano-17α-hydroxy steroid (II) but rather produced it by a different process from a 17(20)-unsaturated steroid.

R. B. Boar, et al., in J.C.S. Perkin I 1242 (1975) reported a 3β-acetoxy-$\Delta^5$-20-acetyl enimide, starting with a pregnenolone derivative. While these compounds are somewhat similar to the enimide (III) of the present invention, the prior art compounds disclose an ester at the 17α position. The present process has the flexibility to produce the enimide (III) where the $C_{17}$ hydroxyl group is protected with an ether not an ester (acetate). The ester protecting group of the prior art processes has the disadvantage of being difficult to remove, whereas, the $C_{17}$ ethers of the present invention do not have that problem. Again, the enimide produced by Boar, et al. was produced from a different starting material by a process different than that of the present invention, i.e. the transformation of the 17-protected 17β-cyano-17α-hydroxy steroid (II) to the enimide (III).

The $\Delta^{20}$-enamide acylate (IV) is known where the steroid A-ring is 3β-hydroxy-$\Delta^5$ (C). Boar et al. produced their $\Delta^{20}$-enamide acylate from the corresponding 3β-acetyl-$\Delta^5$-enimide by reaction with acetic acid containing trichloroacetic acid. See R. B. Boar, et al., J.C.S. Perkin I 1242 (1975). That compound had no substitution in the C-ring. The $\Delta^4$-3-keto-(A) and $\Delta^{1,4}$-3-keto-(B)-$\Delta^{20}$-enamide acylates of the present inventions are easier to convert to the commercial corticoid products than is the compound dislosed by Boar, et al.

The $\Delta^{20}$-enamide (V) is a tautomer of the enimide (III). Boar, supra, disclosed a $\Delta^{20}$-enamide. That compound, compound IV on p. 1243, differs from the $\Delta^{20}$-enamide (V) in that at $C_{17}$ the group is an ester, whereas, the $\Delta^{20}$-enamides (V) must have an ether or hydroxy group at $C_{17}$. It has been found that use of ethers at $C_{17}$ (—OZ) permit the reaction of the 17-protected-17β-cyano-17α-hydroxy steroid (II) with Grignard reagents to produce the enimide (III) and further the $\Delta^{20}$-enamide (V). D. H. R. Barton, et al., J.C.S. Chem. Comm. 774 (1981) also discloses a $\Delta^{20}$-enamide 17-acetate, see compound (5). That compound further differs from the $\Delta^{20}$-enamides (V) of the present invention in that the substituent on the enamide nitrogen atom is an aldehyde (a formyl group) in Barton but is an acyl group in the present invention.

Boar, supra, discloses the transformation of an enimide-17-ester to a $\Delta^{16}$-progesterone. The process of the present invention involves the transformation of an enimide-17α-ether (III, Z is not a hydrogen atom) or its tautomer, a $\Delta^{20}$-enamide-17-ether (V) to a $\Delta^{20}$-enamide 17-ester (IV), by an ether to ester exchange followed by hydrolysis to give a progesterone 17-acylate (VI). Boar discloses the hydrolysis of an enimide 17-acetate to a 20-keto-17-acetate (VI). The process of the present invention does not include the enamide 17-acetate of Boar or the process of its formation.

The oxazoline (IX), structure type, is known, see Great Britain Pat. No. 2,086,907A and J.C.S. Chem. Comm. 774 (1981). D. H. R. Barton, et al. in J.C.S. Chem. Comm. 774 (1981) transformed a $\Delta^{17(20)}$-20-amide to the oxazoline by reactions with a peracid whereas the process of the present invention starts with an enimide (III). Barton, et al. proposed a mechanism for his reaction involving an 17,20-epoxide and a 17α-hydroxy-20-enimide. However, none of the intermediates were isolated, identified or the mechanism proved. The 21-bromo-20-formaldimine 17-acetate (XVI) is disclosed by Barton, supra.

The 21-halo-$\Delta^{20}$-enamides (XX) are not known. The unhalogenated $\Delta^{20}$-enamide 17-acylate is known where the steroid A-ring is of the 3β-hydroxy-$\Delta^5$ series, see Boar and Barton supra. With ether substitution at C-17, the unhalogenated $\Delta^{20}$-enamide 17-ethers are unknown regardless of the substitution in the A-ring.

By the process of the present invention the $\Delta^{20}$-enamide (V) is converted into the corresponding 21-halo enimide (XV) in a one-step process. D. M. R. Barton, et al., JCS Chem. Comm., 774 (1981) disclosed the transformation of a $\Delta^{20}$-enamide (5), where the nitrogen was substituted with a formamide to the 21-bromo enimide (6) where both contain the 17-acetate.

The 21-halo enimide (XV) can be transformed to the 17α-hydroxy-21-bromo steroid (XIII) directly or indirectly via the 21-halo-$\Delta^{20}$-enamide (XX). Barton, supra, disclosed transformation of the 21-bromo steroid (7) to the 21-bromo-20-keto steroid (8) in which the ester at C-17 was not lost. The process of the present invention produces the free 17α-hydroxy-21-bromo-20-keto steroid (XIII).

BRIEF DESCRIPTION OF THE INVENTION

Disclosed are 17β-cyano-17α-hydroxy (IB), 17-protected-17β-cyano (IIB), enimide (II A-C), $\Delta^{20}$-enamide (V A-C), 21-haloenimide (XV A-C), 21-halo-$\Delta^{20}$-enamide (XX A-C), $\Delta^{20}$-enamide acylate (IV A,B), 17β-cyano-17α-hydroxy (IC) and 17β-cyano-17α-hydroxy (IA') steroids.

Disclosed is a process for the preparation of a $C_3$ protected form of an enimide (III A-C) which comprises (1) contacting a $C_3$ protected form of a 17-protected-17β-cyano-17α-hydroxy steroid (II A-C) with a methylating agent and contacting the product of step (1) with an acylating or silating agent.

Also disclosed is a process for the preparation of a $C_3$ protected form of a $\Delta^{20}$-enamide acylate (IV A-C) which comprises contacting a steroid selected from the group consisting of a $C_3$ protected form of an enimide (III A-C) or a $C_3$ protected form of a $\Delta^{20}$-enamide (V A-C) with a carboxylic acid of the formula $R_{17}COOH$ and an anhydride of the formula $(R_{17}CO)_2O$ where $R_{17}$ is a hydrogen atom alkyl of 1 thru 5 carbon atoms, phenyl substituted with zero thru 2 chlorine atoms, trichloromethyl or trifluoromethyl groups.

Further disclosed is a process for the preparation of a $C_3$ protected form of a $\Delta^{20}$-enamide (V A-C) which comprises contacting a $C_3$-protected form of an enimide (III A-C) with an acid or base.

Also disclosed is a process for the preparation of a $C_3$ protected form of an oxazoline (IX A-C) which comprises contacting a steroid selected from the group consisting of a $C_3$ protected form of an enimide (III A-C) or a $C_3$ protected form of a $\Delta^{20}$-enamide (V A-C) with an acid in an organic solvent or mixtures thereof.

Further disclosed is a process for the preparation of a steroid selected from the group consisting of a $C_3$ protected form of a 21-halo enimide (XV A-C) and a $C_3$ protected form of a 21-halo-$\Delta^{20}$-enamide (XX A-C) which comprises contacting a $C_3$ protected form of a $\Delta^{20}$-enamide (V A-C) with a halogenating agent.

Further disclosed is a process for preparing a $C_3$ protected form of a 17α-hydroxy steroid (XIII A-C) which comprises (1) contacting a steroid selected from the group consisting of a $C_3$ protected form of a 21-halo enimide (XV A-C) or a $C_3$ protected 21-halo-$\Delta^{20}$-enamide (XXA-C) with an aqueous acid.

DETAILED DESCRIPTION OF THE INVENTION

The 17-keto steroid starting materials are well known to those skilled in the art or can readily be prepared from known compounds by methods will known to those skilled in the art. These include $\Delta^4$-3-keto (A), $\Delta^{1,4}$-3-keto (B) and 3β-hydroxy-$\Delta^5$ (C) steroids, see Chart G. The 17-keto starting materials can be substituted at $C_6$, $C_9$, $C_{11}$ and/or $C_{16}$, with $R_6$, $R_9$, $R_{11}$ and $R_{16}$ as defined infra.

The A-ring of the 17-keto starting material does not have to be protected to form the 17β-cyano-17α-hydroxy steroid (I). However, during the methylation reaction of transforming the 17-protected-17β-cyano-17α-hydroxy steroid (II) to the enimide (III) the A-ring must be protected.

For the $\Delta^4$-3-keto steroids (A) the $C_3$ ketone is protected as the enol ether (Aa), ketal (Ab), or enamine (Ac) as is well known in the art, see Chart H. The preferred enol ether (Aa) is the methyl or ethyl ether. The preferred ketal (Ab) is the ethylene ketal. The preferred enamines are selected from the group consisting of pyrrolidine, morpholine and diethylamino amines. The enol ethers (a) are prepared by methods well known in the art, See J. Org. Chem. 26, 3925 (1961), Steroid Reactions, Edited by Carl Djerassi, Holden-Day, San Francisco, 1962, p. 42–45, and U.S. Pat. No. 3,516,991 (Preparation 1). The ketals (b) are also prepared by well known methods, see Steroid Reactions, supra,, p. 11–14. The 3-enamines (c) are also prepared by methods well known in the art, see U.S. Pat. No. 3,629,298 and Steroid Reactions, supra, p. 49–53.

The $\Delta^{1,4}$-3-keto steroids (B) are protected by reacting the 17-protected-17β-cyano-17α-hydroxy steroid (II) with a strong base such as LDA (lithium diisopropyl amide) to form an enolate represented by formula (Ba). The enolate is then methylated and acylated or silated to form the enimide (III). In the process the 3-enolate is also acylated or silated to give the 3-acylate or 3-silyl derivative of (Ba). In a subsequent workup and hydrolysis the A-ring enolate reforms the $\Delta^{1,4}$-3-keto (B) A-ring functionality.

The 3-hydroxy steroid (C) should have the 3β-hydroxyl group protected as the ether (Ca), see Chart H.

The $C_3$ protected forms (Aa, Ab and Ac) of the $\Delta^4$-3-keto steroids (A), the $C_3$ protected forms (Ba) of the $\Delta^{1,4}$-3-keto steroids (B) and the $C_3$ protected forms (Ca and Cb) of the 3β-hydroxy steroids (C) are considered equivalent to the non-protected or free form (A, B and C) respectively since the $C_3$ protecting groups are readily removable to convert the $C_3$ protected forms (Aa, Ab, Ac, Ba and Ca) to the free or unprotected forms (A, B and C) respectively. In order to remove the $C_3$ protecting group from the $\Delta^4$-3-keto steroids (A), $\Delta^{1,4}$-3-keto steroids (B) and 3β-hydroxy steroids (C) the reaction conditions would generally also remove the $C_{17}$ protecting group (Z) which is undesirable. Therefore, the $C_3$ protecting group remains during subsequent reactions not because it is needed per se but rather so as not to remove the (Z) protecting group. The $C_3$ and $C_{17}$ protecting groups can readily be removed, if desired, from the intermediates producing 17α-hydroxy-free-A-ring steroids.

The 17-keto steroid starting material is reacted with potassium cyanide and 2-cyano-2-hydroxypropane (acetone cyanohydrin) in an alcoholic solvent such as aqueous methanol to give the desired 17β-cyano-17α-hydroxy steroid (I) with high yields and stereospecificity as is known in the art. The reaction may be heated to 30°–50° if desired.

Before protecting the 17α-hydroxy group of the cyanohydrin (I), it is preferred that the $C_3$ function of the $\Delta^4$-3-keto (A), $\Delta^{1,4}$-3-keto (B) or 3β-hydroxy-$\Delta^5$ (C) steroids be protected as discussed supra although the 17α-hydroxy group may be protected first. 17β-Cyano-17α-hydroxy steroids (I) are known where the 17α-hydroxy group is protected as an ether. See, Steroids 37, 362 (1981) on p 362 for the TMS ether; J. Am. Chem. Soc. 81, 5725 (1959) on p 5726 formula III as the THP ether; Tetra. Lett. 22, 2005 (1971) on p 2007 formula IX as the TMS ether and Japanese Pat. No. 7,062,296 for the butyl vinyl ether. The preferred 17α-protecting group is the ethoxy ethyl ether. Other suitable groups include THP, TMS, methoxymethyl, and butoxy ethyl ethers. The appropriate form of the 17β-cyano-17α-hydroxy steroid (I) is reacted with a reagent to form the desired ether protecting group (Z) such as ethoxy ethyl ether (EEE) using an acid catalyst such as pyridine hydrochloride, p-TSA, or in an inert solvent. Suitable solvents include toluene, SSB, cyclohexane, methylene chloride.

The enimide (III) and the $\Delta^{20}$-enamide (V) are tautomers. The 17-protected-17β-cyano-17α-hydroxy steroid (II) can be converted to both the enimide (III) and the $\Delta^{20}$-enamide (V). The 17-protected-17β-cyano-17α-hydroxy steroid (II) is converted to the enimide (III) by first reaction with a methylating agent. Addition of the methylating agent to the protected cyanohydrin (II) gives an intermediate imine which can be isolated, but it is preferred to acylate or silate the imine anion in situ by addition of an acylating or silating agent. The acylating agents are selected from the group consisting of acyl halides and acyl anhydrides of the formulas $R_{20}J$, $(R_{20})_2O$, or $R_{20}''J$. Suitable solvents for this reaction include ethers such as THF. The reaction is performed in the temperature range of about $-30°$ to about $100°$. Silating agents include $J$-$Si(CH_3)_3$ and $J$-$Si(CH_3)_2C(CH_3)_3$.

Some methylating agents have greater Lewis acid properties or form better Lewis acids after methylation than other methylating agents. For example, methyl Grignard is a better Lewis acid than methyl lithium. Methylating agents such as methyl Grignard having sufficient Lewis acidity transform the initially formed enimide (III) to its tautomeric form the $\Delta^{20}$-enamide (V). Thus, with the methylating agents which are Lewis acids, such as methyl magnesium chloride the ratio of tautomeric products, the enimide (III) and $\Delta^{20}$-enamide (V) is time dependent. At short time periods the predominate product is the enimide (III). With time there is a decrease in the amount of enimide (III) and increase the amount of $\Delta^{20}$-enamide (V) to the point where predominately the $\Delta^{20}$-enamide (V) is present. Methylating agents which are poor Lewis acids include, for example, methyl lithium. The 17-protected-17β-cyano-17α-hydroxy steroid (II) is transformed to the enimide (III) if the methylating agent is methyl lithium and the imine anion formed is acylated or silated. Methylating agents which are or produce Lewis acids include Grignard reagents, for example, methyl magnesium bromide, chloride and iodide. For example, if the methylating agent is methyl magnesium bromide and the acylating agent is acetic anhydride, during the methylation/acylation step of transforming the 17-protected-17β-cyano-17α-hydroxy steroid (II) to the enimide (III) the methyl magnesium bromide is transformed to magnesium bromoacetate which is a (Lewis) acid and therefore the enimide (III) which is initially produced is transformed to the $\Delta^{20}$-enamide (V) without addition of another acid, see Example 7. If it is desired to isolate the enimide (III) the preferred methylating agent utilized in the methylation reaction is one that in situ will not be transformed to a Lewis acid. Methyl lithium is a methylating agent operable in effectuating the methylation reaction but will not form a Lewis acid and will permit isolation of the enimide (III), see Examples 5 and 31. The preferred methylating reagent is methyl lithium.

The enimide (III) is isomerized to its tautomer the $\Delta^{20}$-enamide (V) by reaction with an acid, or a base. Acids include Lewis acids, and carboxylic acids including polycarboxylic acids. It is preferred that the acid be acetic, propionic, benzoic or citric. The most preferred acid is acetic acid. Bases which are operable include guanidine and amidine bases, preferred are DBU and DBN.

The enimide (III) and $\Delta^{20}$-enamide (V) are tautomers. Both can be transformed to corresponding $\Delta^{20}$-enamide 17-ester (IV) by reaction with a carboxylic acid of the formula $R_{17}COOH$ and a carboxylic acid anhydride of the formula $(R_{17}CO)_2O$ in the acid as solvent in the temperature range of about $0°$ to about $80°$ preferably at about $20°$ to about $25°$. The reaction converts the protecting group "Z" at C-17 to the 17-ester ($-OCOR_{17}$) and with the enimide (III) also the enimide portion is tautomerized to the $\Delta^{20}$-enamide. It is preferred that $R_{17}$ is methyl, ethyl or phenyl, more preferably methyl. If $R_{17}$ is a hydrogen atom, trichloromethyl, trifluoromethyl or an equivalent substituent which makes the ester $R_{17}COO-$ active, such ester (IV) may be selectively removed with mild base such as bicarbonate in methanol to give the 17α-hydroxy-$\Delta^{20}$-enamide (XVII). Likewise the 21-halo steroid (XI) can be converted to the 21-halo-17α-hydroxy corticoid (XIII). Alternatively, if $R_{17}$ is trimethyl silyl or other convenient silyl protecting group, such group may be removed with mild base as above, mild acid or fluoride ion producing the desired 17α-hydroxy group in XVII.

The $\Delta^{20}$-enamide (V) can be transformed to the 17α-hydroxyprogesterone 17-ester (VI) by reaction with an appropriate esterifying agent such as an anhydride $(R_{17}CO)_2O$ and the corresponding carboxylic acid $R_{17}COOH$ to produce the enamide acylate (IV) followed by addition of water to hydrolyze the enamide acylate (IV) to the 17α-hydroxyprogesterone 17-ester (VI).

The enimide (III) can be readily transformed to a 17α-hydroxyprogesterone 17-ester (VI) by reaction with the appropriate esterifying agent such as an anhydride $(R_{17}CO)_2O$ or acid halide $R_{17}COJ$ in the corresponding acid, $R_{17}COOH$, solvent. Preferred is acetic anhydride in acetic acid followed by water. This in situ acetylation avoids an often difficult separate acylation step on the hindered tertiary 17α-hydroxy group, see U.S. Pat. No. 4,154,748. If one were to start with androstenedione as the 17-ketone and perform the process of the present invention using acetic anhydride/acetic acid in converting the enimide (III) or $\Delta^{20}$-enamide (V) to the $\Delta^{20}$-enamide acylate (IV), one would obtain on hydrolysis 17α-hydroxyprogesterone 17-acetate (VI'A) as the 17α-hydroxyprogesterone 17-ester (VI), see Chart B. The 17α-hydroxyprogesterone 17-acetate (VI'A) can be transformed to 17α-hydroxy-6-methyleneprogesterone 17-acetate (VII) by the process of U.S. Pat. No. 3,642,840, Example 11 which can be transformed to 17α-hydroxy-6α-methylprogesterone 17-acetate (VIII) which is medroxyprogesterone by the process of U.S. Pat. No. 3,679,715, Example 1.

Alternatively, by starting with 6α-methylandrost-4-ene-3,17-dione (U.S. Pat. No. 3,166,551, Example 8) as the 17-keto steroid and performing the process of the present invention using acetic anhydride/acetic acid as the acetylating agent, 17α-hydroxy-6α-methylprogesterone 17-acetate (VIII) is obtained directly.

Just as the tautomers, the enimide (III) and $\Delta^{20}$-enamide (V) can both be transformed to the corresponding $\Delta^{20}$-enamide 17-ester (IV), likewise they both can readily be converted to the oxazoline (IX) by contacting the tautomer with an acid in an organic solvent. Mineral, Lewis, or organic acids are suitable. This would include sulfuric, hydrochloric, phosphoric and equivalent inorganic acids. Organic acids such as p-TSA and carboxylic ($R_{17}COOH$) and dicarboxylic acids such as oxalic acid also are operable and are preferred. Suitable organic solvents include, for example, toluene, methylene chloride, ethyl acetate, methanol, ethanol, THF, diethyl ether, and mixtures thereof. The enimide (III) or $\Delta^{20}$-enamide (V) is contacted with the acid in the suitable organic solvent in a temperature range of about 20° to about 60°. The reaction mixture can be heated to the reflux temperature of the particular solvent used. The reaction is monitored by TLC and when complete the oxazoline (IX) is isolated by means well known to those skilled in the art or can be halogenated without isolation.

The oxazoline (IX) is a very useful intermediate in the production of corticoid diesters (XII), see Chart C. The oxazoline (IX) is halogenated to produce the halooxazoline (X) according to the procedure set forth in J.C.S. Chem. Comm. 774 (1981). The halooxazoline (X) is then readily converted by hydrolysis to the 21-halo steroid (XI) which is readily transformed to the pharmacologically useful corticoid diester (XII). Alternatively, the 21-halo enimide (XV) and 21-halo-$\Delta^{20}$-enamide (XX) is readily converted into halooxazoline (X) by contacting with an acid in an organic solvent.

The $\Delta^{20}$-enamide (V) can be readily converted to the corresponding 21-halo enimide (XV) by reaction with a halogenating agent selected from the group consisting of bromine, pyridine hydrobromide perbromide, NBS, dibromantin and NCS. The 21-halo enimide (XV) can be converted into its tautomer, 21-halo-$\Delta^{20}$-enamide (XX) under the influence of acid or base. Acids include organic carboxylic acids or polycarboxylic acids either as the solvent or in suitable organic solvents such as THF, toluene or methylene chloride. Acids may include Lewis acids such as $BF_3\sim$etherate in organic solvent. Bases which are operable include amidine bases. Preferred are DBU and DBN. Under certain conditions the halogenation reaction becomes sufficiently acidic or basic to cause tautomerization of the 21-halo enimide (XV) to the 21-halo-$\Delta^{20}$-enamide (XX).

The 21-haloenimide (XV) and/or the 21-halo-$\Delta^{20}$-enamide (XX) can be hydrolyzed under acidic conditions to either the 21-halo steroid (XI) or the 21-halo-17α-hydroxy corticoid (XIII) depending on the conditions chosen. To prepare the corticoid diester (XII), the 21-haloenimide (XV) or its tautomer 21-halo-$\Delta^{20}$-enamide (XX) is first hydrolyzed with relatively high concentrations of aqueous acid with an organic cosolvent. The acids include mineral acids and carboxylic acids such as sulfuric, acetic, hydrochloric, etc. Organic cosolvents include methanol, toluene, methylene chloride. The 21-halo steroid (XI) is then converted to the corticoid diester (XII) by treatment with acylate ion in an organic solvent. The preferred conditions are treatment of the 21-halo steroid (XI) with potassium acylate in a mixture of DMF and toluene at 50°-100° for 6-18 hr. Specifically, to prepare the 17,21-diacetate (XII) the 21-halo steroid (XI) is treated with potassium acetate in DMF and toluene at 75° for 18 hr. The corticoid diesters (XII) are important pharmaceuticals, such as betamethasone dipropionate and diflorasone diacetate, and important intermediates such as Reichstein's Compound S 17,21-diacetate which is converted to hydrocortisone 17,21-diacetate by fermentation. The corticoid diesters (XII) can be converted to the commercially important 17,21-dihydroxy corticoids by base hydrolysis. For example, hydrocortisone diacetate formula XII where $R_{11}$ is β-hydroxyl, $R_6$, $R_9$ and $R_{16}$ are hydrogen atoms can be converted to hydrocortisone by treatment with methanolic potassium carbonate at 20°-25°. Hydrocortisone can be converted to hydrocortisone 21-acetate by reaction with acetic anhydride in pyridine as is well known to those skilled in the art.

To prepare the commercially important corticoid 21-ester (XIV) directly from the 21-halo-$\Delta^{20}$-enamide (XX) or the 21halo enimide (XV) the 21-halo compounds are hydrolyzed with dilute aqueous inorganic mineral acids such as sulfuric, hydrochloric or phosphoric in an organic solvent. The preferred conditions include treatment of (XV) or (XX) with dilute aqueous sulfuric acid in THF (Example 21) producing the 21-halo-17α-hydroxy corticoid (XIII). The 21-halo-17α-hydroxy corticoid (XIII) is converted to the corticoid 21-ester (XIV) by treatment with acylate ion as is well known to those skilled in the art.

DEFINITIONS

The definitions and explanations below are for the terms as used throughout the entire patent application including both the specification and the claims.

All temperatures are in degrees Centigrade.
TLC refers to thin-layer chromatography.
IR refers to infrared spectroscopy.
UV refers to ultraviolet spectroscopy.
CMR refers to C-13 magnetic resonance spectroscopy, chemical shifts are reported in ppm (δ) downfield from TMS.
NMR refers to nuclear (proton) magnetic resonance spectroscopy, chemical shifts are reported in ppm (δ) downfield from TMS.
TMS refers to tetramethylsilane.
MS refers to mass spectrometry expressed as m/e or mass/change unit.
When solvent pairs are used, the ratio of solvents used are volume/volume (v/v).
THF refers to tetrahydrofuran.
DMF refers to dimethylformamide.
SSB refers to an isomeric mixture of hexanes.
p-TSA refers to p-toluenesulfonic acid monohydrate.
Hal is a chlorine, bromine, iodine, atom.
NBS refers to N-bromosuccinimide.
NCS refers to N-chlorosuccinimide.
TMS refers to tetramethylsilyl
THP refers to tetrahydropyronyl
EEE refers to ethoxy ethyl ether ($-O-CH_2CH_2OCH_2CH_3$).
DBU refers to 1,8-diazabicyclo[5.4.0]undec-7-ene.
DBN refers to 1,6-diazabicyclo[3,4,0]non-5-ene.
LDA refers to lithium diisopropyl amide.
MEM refers to 2-methoxyethoxymethyl ($CH_3OCH_2CH_2OCH_2O-$).
Androstenedione refers to androst-4-ene-3,17-dione.
When the term "alkyl of ___ thru ___ carbon atoms" is used, it means and includes isomers thereof where such exist.
R refers to alkyl 1 thru 5 carbon atoms or a hydrogen atom with the proviso that the R's can be the same or different.

$R_a$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine.

$R_g$ is $R_a$, a hydrogen atom or phenyl.

$R_3$ is alkyl of 1 thru 5 carbon atoms with the proviso that for the ketal (Ab) and the enamine (Ac); the $R_3$ groups can be connected and when connected may be connected by an oxygen or nitrogen atom.

$R_6$ is a hydrogen or fluorine atom or methyl group.

$R_9$ is nothing, a hydrogen, fluorine or oxygen atom which makes the C ring
 (a) $\Delta^{9(11)}$ when $R_9$ is nothing and
 (b) $9\beta,11$-epoxide when $R_9$ is an oxygen atom.

$R_{11}$ is a hydrogen or oxygen atom, two hydrogen atoms, or $\alpha$- or $\beta$-hydroxyl group which makes the C-ring
 (a) $\Delta^{9(11)}$ when $R_{11}$ is a hydrogen atom,
 (b) $9\beta,11\beta$-epoxide when $R_{11}$ is an oxygen atom and .... between $C_{11}$ and $R_{11}$ is a single bond, and
 (c) a ketone when $R_{11}$ is an oxygen atom and .... between $C_{11}$ and $R_{11}$ is a double bond.

$R_{16}$ is a hydrogen atom or methyl group.

$R_{17}$ is a hydrogen atom alkyl of 1 thru 5 carbon atoms, phenyl substituted with zero thru 2 chlorine atoms, trichloromethyl or trifluoromethyl groups.

$R_{17}'$ is a hydrogen atom or trifluoromethyl group.

$R_{20}$ is —OC—$R_{20}'$ or —$R_{20}''$.

$R_{20}'$ is alkyl of 1 thru 5 carbon atoms, phenyl, phenyl substituted 0 thru 2 chlorine atoms, methyl or nitro groups.

$R_{20}''$ is —$Si(CH_3)_3$ or —$Si(CH_3)_2C(CH_3)_3$.

$R_{21}$ is alkyl of 1 thru 5 carbon atoms or phenyl.

$R_{100}$ is alkyl of 1 thru 3 carbon atoms.

$R_{101}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine.

$R_{102}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine.

$R_{103}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine.

$R_{104}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine.

$R_{105}$ is a hydrogen atom or alkyl or 1 thru 3 carbon atoms.

$R_{106}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a secondary amine selected from the group consisting of piperidine, pyrrolidine or morpholine with the proviso that $R_{106}$ and $R_{107}$ combined cannot have more than 14 carbon atoms; $R_{106}$ and $R_{107}$ can be combined to form a secondary cyclic amine selected from the group consisting of piperidine, pyrrolidine and morpholine.

$R_{107}$ is alkyl of 1 thru 7 carbon atoms, cycloalkyl of 5 thru 7 carbon atoms, phenyl substituted with 1 thru 2 —$R_{100}$, —$OR_{105}$ or —$N(R_{105})_2$ where with the amine the $R_{105}$'s can be the same or different and can be combined to form a secondary amine selected from the group consisting of piperidine, pyrrolidine or morpholine with the proviso that $R_{106}$ and $R_{107}$ combined cannot have more than 14 carbon atoms; $R_{106}$ and $R_{107}$ can be combined to form a secondary cyclic amine selected from the group consisting of piperidine, pyrrolidine and morpholine.

J is a chlorine, bromine or iodine atom.

M is a lithium sodium potassium magnesium or calcium atom.

Q refers to a hydrogen atom, or alkyl of 1 thru 5 carbon atoms.

W is a TMS, THP, or EEE group.

X refers to a hydrogen atom or nothing.

Z is selected from the group consisting of a TMS, THP, methoxymethyl, t-butyl-dimethyl silyl and EEE group.

Z' is a hydrogen atom or Z.

$\sim$ indicates that the attached atom or group can be in either the $\alpha$ or $\beta$ configurations.

.... is a single or double bond.

EXAMPLES

Without further elaboration, it is believed that one skilled in the art can, using the preceding description, practice the present invention to the fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

EXAMPLE 1

17$\beta$-Cyano-17$\alpha$-hydroxyandrost-4-en-3-one (IA)

Acetone cyanohydrin (82 ml), potassium cyanide (1 gm) and water (2 ml) are added to a slurry of androst-4-en-3,17-dione (0.80 g) in methanol (400 ml) and water (40 ml) at 35°. The reaction becomes homogeneous and on continued stirring a heavy slurry develops. After 3 hours, 120 ml of water is added dropwise, and the slurry allowed to stir overnight at 20°–25°. The slurry is then cooled in an ice bath, filtered, and the solids washed with methanol/water (1/1). The solvents are dried under reduced pressure to give 70.4 g of the title compound. An additional 13.17 g of product is isolated from the mother liquor on partial evaporation, m.p.=159°–160.5°; $[\alpha]^D(c=1, CHCl_3)=+145.9°$; MS=313, 298, 286, 245 and 124 m/e; NMR $(CDCl_3)=1.00, 1.20, 3.5$ and $5.72$ $\delta$

EXAMPLE 2

17β-Cyano-17α-hydroxyandrosta-4,9(11)-dien-3-one (IA)

Acetone cyanohydrin (5 ml) and sufficient potassium cyanide to adjust the pH to 9.9 is added to a slurry of androst-4,9(11)-dien-3,17-dione (0,5 g), methanol (40 ml) and water (2.5 g) at 40°. The reaction becomes homogeneous followed by precipitation of the product. After 3.5 hours, water (7.5 ml) is added dropwise and the reaction is allowed slowly to stir at 20°–25° overnight. The slurry is cooled on in ice bath, filtered, the solids washed with methanol/water (1/1) and dried under reduced pressure to give the title compound (4.54 g); $[\alpha]^D$(c=1, CHCl$_3$)= +118°; MS=311, 296 and 284 m/e; NMR (CDCl$_3$)=0.97, 1.37, 2.9, 5.5 and 5.70 δ

EXAMPLE 3

17β-Cyano-17α-hydroxyandrost-5-en-3-ethylidine ketal (IAb)

p-TSA (100 mg) is added to a mixture of 17β-cyano-17α-hydroxyandrost-4-en-3-one (IA, Example 1, 5 g) in methylene chloride (50 ml), ethylene glycol (5 ml) and trimethylorthoformate (2.5 ml). The resulting mixture is stirred 2 hours at 20°–25°. The reaction mixture is concentrated to approximately 20 ml at atmospheric pressure. Triethylamine (0.2 ml) is added, the mixture extracted with phosphate buffer (pH 7) and the organic phase concentrated to a solid. The solid is crystallized from methanol to give the title compound (5.1 g); m.p.=229.5°–230.5°; $[\alpha]^D$(c=1, CHCl$_3$)= +4.2°; MS=357, 342, 330 and 302 m/e; NMR (CDCl$_3$)=0.93; 1.10, 3.3, 3.97 and 5.3 δ

EXAMPLE 4

17β-Cyano-17α-(α-ethoxyethyl)-etherandrost-5-en-3-ethylidine ketal (IIAb)

A mixture of 17β-cyano-17α-hydroxyandrost-5-en-3-ethylidine ketal (IAb, Example 3, 3.57 g) in methylene chloride (10 ml) containing ethyl vinyl ether (2 ml) and pyridine hydrochloride (100 mg) is heated in a sealed bottle at 40° for 2.5 hours and at 40° for 4 hours. Triethylamine (0.2 ml) is added and the reaction washed with phosphate buffer (pH 7), water and then dried over sodium sulfate, filtered and the filtrate concentrated under reduced pressure to give the title compound (4.61 g) as an oily mixture of diastereomers; NMR (CDCl$_3$)=0.98, 1.04, 3.5, 3.94, 5.0 and 5.2 δ

EXAMPLE 5

17α-(α-ethoxyethyl)-ether-20-acetyliminopregn-5-en-3-ethylidine ketal (IIIAb)

Methyl lithium (1.5M, 1.2 ml) is added to a mixture of 17β-cyano-17α-(α-ethoxy ethyl)-ether-androst-5-en-3-ethylidine (IIAb, Example 4, 550 mg) and toluene (3.5 ml) at 0°. After 2.5 hours at 0° the reaction is quenched by adding acetic anhydride (1 ml) and toluene (1 ml) resulting in a stirrable gel. Aqueous phosphate buffer (pH 7) is added, the phases are separated and the the lower aqueous phase is backwashed with ethyl acetate. The combined organic phases are backwashed with sodium bicarbonate (5%), phosphate buffer, dried over sodium sulfate and concentrated to give the title compound (643 ml) as an oil; NMR (CDCl$_3$)=0.71, 1.02, 1.92, 2.00, 2.12, 3.4, 3.93, 4.7 and 5.3 δ; MS=487, 415 and 297 m/e

EXAMPLE 6

17α-(α-ethoxyethyl)-ether-20-acetylaminopregna-5,20-dien-3-ethylidine ketal (VAb)

17α-(α-ethoxyethyl)-ether-20-acetylaminopregna-5-en-3-ethylidine ketal (IIIAb, Example 5, 3 mM) is stirred in glacial acetic acid (2 ml) for 1.5 hour at 20°–25°. Toluene is added and the organic diluents removed under reduced pressure. Additional toluene is added and the mixture washed with sodium bicarbonate (5%), phosphate buffer and the organic phase is dried over sodium sulfate and concentrated under reduced pressure to give the title compound (1.7 g) as an oil, NMR (CDCl$_3$)=0.69, 1.02, 2.03, 3.4, 3.94, 4.6, 4.82, 4.97, 5.3, 5.84, 6.03 and 6.8 δ

EXAMPLE 7

17α-(α-ethoxyethyl)-ether-20-acetylaminopregna-5,20-dien-3-ethylidine ketal (VAb)

Methyl magnesium bromide in ether (2.85M, 7 ml) is added to a mixture of 17β-cyano-17α-(α-ethoxyethyl)-etherandrost-5-en-3-ethylidine ketal (IIAb, Example 4, 10 mM) in toluene (25 ml) and the mixture heated at 55° for 6 hours in a sealed pressure bottle. The mixture is then dissolved in THF (10 ml) and is added to toluene (20 ml) containing acetic anhydride (3 ml) which had been previously cooled to 0°. This mixture is allowed to warm to 25° during a ½ hour stirring period after which it is extracted with phosphate buffer (twice), dried over sodium sulfate, concentrated to give the title compound as an oil. This product is spectroscopically and chromatographically identical to the product of Example 6.

EXAMPLE 8

17α-Acetoxy-20-acetylaminopregna-5,20-dien-3-ethylidine ketal (IVAb)

17β-Cyano-17α-(α-ethoxy ethyl)-ether androst 5-en-3-ethylidine ketal (VAb, Example 7) is dissolved in glacial acetic acid (10 ml) and acetic anhydride (5 ml) and the mixture stirred for 24 hours at 20°–25°. The reaction mixture is then added to aqueous phosphate buffer and extracted with ethyl acetate. The phases are separated and the organic phase is washed with water, sodium bicarbonate (5%), water again, dried over sodium sulfate and concentrated to give the title compound as an oil; NMR (CDCl$_3$)=0.73, 1.07, 2.08, 3.97, 5.00, 5.3, 5.8 and 6.6 δ; CMR (CDCl$_3$)=169.78, 140.23, 138.85, 121.68, 109.35, 104.01, 93.59 and 64.36 δ; MS=398 (m+1); IR (CHCl$_3$)=1730, 1685 cm$^{-1}$

EXAMPLE 9

17α-Acetoxy-20-acetylaminopregna-5,20-dien-3-ethylidine ketal (IVAb)

Following the general procedure of Example 8 and making noncritical variations, but starting with 17α-(α-ethoxy ethyl)-ether-20-acetylaminopregn-5-en-3-ethylidine ketal (IIIAb, Example 5) the title compound is obtained as an oil identical in all respects to the product of Example 8.

EXAMPLE 10

17α-Acetoxyprogesterone (VIA)

Acetic acid (1.5 ml) and water (0.5 ml) are added to 17α-acetoxy-20-acetylaminopregna-5,20-dien-3-ethylidine ketal (IVAb, Example 8, 0.5 mM) in acetic acid (0.66 ml) and acetic anhydride (0.34 ml). The reaction mixture is heated at 55° for approximately 18 hours. TLC (ethyl acetate/toluene:3/7) shows the hydrolysis to be complete to approximately a 90/10 mixture of 17α-acetoxyprogesterone and 17α-hydroxyprogesterone. Acetic anhydride (0.75 ml) and p-TSA (30 mg) are added and heating continued for 2 hours at 50°. Water (0.3 ml) is added and the heating is continued at 50° for 7.5 hours. Water (2 ml) is then added resulting in a precipitate which is filtered and dried to give the title compound.

EXAMPLE 11

17R,2'-Methyl-4'-methylenespiro-3-ethylenedioxyandrost-5-en-17,5'(4'H)-oxazole (IXAb)

Acetic acid (5 ml) and acetic anhydride (0.4 ml) are added to 17α-(α-ethoxyethyl)-ether-20-acetylaminopregn-5-en-3-ethylidine ketal (IIIAb, Example 5, 10 mM) and the mixture heated to 55°. After 1 hour of heating at 55°, additional acetic acid (5 ml) and acetic anhydride (0.4 ml) are added and the heating continued for an additional 2.5 hours. The reaction mixture is cooled, the solid filtered, washed with diethyl ether and dried to give the title compound (1.45 g), m.p.=199°–209°; NMR (CDCl$_3$)=0.81, 1.03, 2.04, 3.86, 4.65 and 5.30 δ; MS (CI)=398 (M+1)

EXAMPLE 12

17R,2'-Methyl-4'-methylenespiro-3-ethylenedioxyandrost-5-en-17,5'(4'H)-oxazole (IXAb)

Methanol (2 ml) and p-TSA.H$_2$O (2 ml) is added to 17α-(α-ethoxyethyl)-ether-20-acetylaminopregn-5,20-dien-3-ethylidine ketal (VAb, Example 6, 200 ml) and the mixture heated to 70° for 40 minutes. Analysis by TLC and NMR shows that the product is mostly the title compound along with small amounts of 3-methyl enol ether and Δ4-3-keto analogues.

EXAMPLE 13

17R,2'-Methyl-4'-bromomethylenespiro-3-ethylenedioxyandrost-5-en-17,5'(4'H)-oxazole (XAb)

Pyridium bromide perbromide (3 ml) is added to 17R,2'-methyl-4'-methylenespiro-3-ethylenedioxyandrost-5-en-17,5'(4'H)-oxazole (IXAb, Example 11, 50 ml) in methylene chloride (1 ml) and pyridine (0.05 ml) at 0°. TLC shows a single less polar product. A few drops of sodium bisulfite (1M) and acetic acid are added. The phases are separated and the organic phase is washed with water, dried over sodium sulfate, and concentrated to give the title compound, NMR (CDCl$_3$)=0.92, 1.03, 2.17, 3.93, 5.27 and 5.33 δ; MS (CI,CH$_4$)=476, 478 (M+1), 396

EXAMPLE 14

21-Bromo-17α-acetoxyprogesterone (XIA)

17R,2'-Methyl-4'-bromomethylenespiro-3-ethylenedioxyandrost-5en-17,5'(4'H)-oxazole (XAb, Example 13). The product from Example 13 is dissolved in a solution of acetic acid (0.75 ml) and water (0.25 ml) and heated overnight at about 105° in a sealed vial. The reaction mixture is then added dropwise to a solution of phosphate buffer (pH 7) giving the title compound, NMR (CDCl$_3$)=0.72, 1.17, 2.10, 3.90 and 5.67 δ

EXAMPLE 15

21-Bromo-17α-(α-ethoxyethyl)-ether-20-acetyliminopregna-5-en-3-ethylidine ketal (XVAb)

Pyridinium hydrobromide perbromide (0.29 g) is added to 17α-(α-ethoxy ethyl)-ether-20-acetylaminopregna-5,20-dien-3-ethylidine ketal (VAb, Example 6, 411 mg) in a mixture of methylene chloride (3 ml), methanol (0.75 ml), water (0.12 ml) and triethylamine (0.26 ml) at 0°. The reaction is complete after about 5 minutes. Methylene chloride and water are added, the phases separated, the organic phase is dried over sodium sulfate and concentrated to give the title compound, NMR (CDCl$_3$)=0.77, 0.83, 1.03, 2.27, 2.29, 3.9 and 5.27 δ; MS (CI)=566 and 568 (m+1) and 550.

EXAMPLE 16

21-Bromo-17α-acetoxy-20-acetylaminopregn-5-en-3-ethylidine ketal (XVIAb)

Pyridinium hydrobromide perbromide (100 ml) is added to 17α-acetoxy-20-acetylaminopregn-5,20-diene-3-ethylidine ketal (IVAb, Example 8, 140 ml), and the mixture is stirred for 15 minutes at 0°. Phosphate buffer (pH 7) is added, the phases are separated and the organic phase is washed with sodium bicarbonate (5%), water, dried over sodium sulfate and concentrated to an oil. The oil is chromatographed over silica gel (10 gm) eluting with acetone/methylene chloride: 5/95, the appropriate fractions are pooled and concentrated to give the title compound; NMR (CDCl$_3$)=0.82, 1.03, 2.07, 2.30, 3.9, and 5.28 δ; MS (CI)=536 and 538 (m+1).

EXAMPLE 17

21-Bromo-17α-acetoxy-20-acetylaminopregna-5,20-dien-3-ethylidine ketal (XXIAb)

DBW (0.5 ml) is added to 21-Bromo-17α-acetoxy-20-acetylaminopregn-5-en-3-ethylidine ketal (XVIAb, Example 16, 3.16 g) and toluene (8.5 ml). After ½ hour the tautomerization is complete. The reaction mixture is washed with phosphate buffer (pH 7), filtered through magnesol, dried over sodium sulfate and concentrated to give the title compound; NMR (CDCl$_3$)=0.72, 0.77, 1.03, 2.03, 2.06, 3.93, 4.52, 4.80, 5.3, 6.3, 6.4, 6.5 and 7.6 δ

EXAMPLE 18

21-Bromo-17α-acetoxyprogesterone (XIA)

Following the general procedure of Example 19 and making noncritical variations, but starting with 21-bromo-17α-acetoxy-20-acetylaminopregna-5,20-dien-3-ethylidine ketal (XXIAb, Example 17), the title compound is obtained.

EXAMPLE 19

21-Bromo-17α-acetoxyprogesterone (XIA)

Acetic acid (1.5 ml) and water (0.5 ml) are added to 21-bromo-17α-acetoxy-20-acetylamino-pregn-5-en-3-ethylidine ketal (XVIAb, Example 16, 38 mg). The mixture is heated in a sealed vial at 108° for one hour. Toluene is added to the cooled reaction mixture, the phases separated, the organic phase washed with water, dried over sodium sulfate and concentrated under reduced pressure to give the title compound, NMR (CDCl$_3$)=0.73, 1.20, 2.10, 3.93, and 5.67 δ

EXAMPLE 20

17α,21-Dihydroxypregn-4-en-3,20-dione 17,21-diacetate (XIIA)

21-Bromo-17α-acetoxyprogesterone (XIA, Example 19, 50 mg) is dissolved in toluene (0.3 ml) and DMF (0.3 ml) with acetic acid (4 micro liters) and stirred with potassium acetate (19 mg) at 70° in a sealed vial for 22½ hours. Additional toluene is added and the mixture extracted with water. The organic phase is dried over sodium sulfate and concentrated under reduced pressure to give the title compound. NMR (CDCl$_3$) 0.76, 1.20, 2.07, 2.13, 4.55, 5.85 and 5.67 δ

EXAMPLE 21

21-Bromo-17α-hydroxyprogesterone (XIIIA)

Sulfuric acid (1N, 1 drop) is added to 21-bromo-17α-(α-ethoxyethyl)-ether-20-acetylaminopregn-5-en-3-ethylidine ketal (XVAb, Example 15, 50 mg) in THF (0.6 ml) and water (0.2 ml). This mixture is stirred at 20°-25° for 18 hours and then heated at 60° for 17.5 hours to give the title compound, NMR (CDCl$_3$)=0.73, 1.20, 4.22, and 5.70 δ

EXAMPLE 22

21-Bromo-17α-hydroxypregn-5-en-20-one 3-ethylidine ketal (XIIIAb)

Sulfuric acid (1N, 4 drops) is added to 21-bromo-17α-(α-ethoxyethyl)-ether-20-acetylaminopregn-5-en-3-ethylidine ketal (XVAb, Example 15, 220 mg) in THF (2.5 ml) and water (0.8 ml). The mixture is stirred at 20°-25° for four days. Toluene is added and the reaction mixture washed with buffer (pH 7), dried over sodium sulfate and concentrated to an oil. The oil is chromatographed on a silica gel column diluting with ethyl acetate/hexane: 1/1. The appropriate fractions are pooled and concentrated to give the title compound, NMR (CDCl$_3$)=0.68, 1.02, 3.91, 4.25, and 5.30 δ; MS (CI)=453, 455 (m+1), 435, 437, 373, 357, and 355.

EXAMPLE 23

21-Bromo-17α-hydroxyprogesterone (XIIIA)

21-Bromo-17α-hydroxypregn-5-en-20-on-3-ethylidine ketal (XIIIAb, Example 22) is converted to the title compound by heating the reaction mixture of Example 22 to 60° for about 18 hours instead of stirring at 20°-25° for four days.

EXAMPLE 24

17β-Cyano-3β,11β,17α-trihydroxyandrosta-3,5-diene 3-methyl ether (IAa)

Pyridine hydrochloride (120 mg), methanol (20 ml) and trimethyl orthoformate (3 ml) are added to 17β-cyano-11β,17α-dihydroxyandrost-4-en-3-one (IA, Example 25, 6.58 g). The mixture is heated at reflux overnight, cooled to crystallize and reheated for 1.5 hours at 50°-55°. The solid is filtered, washed with buffer (pH 7), water and dried to give the title compound.

EXAMPLE 25

17β-Cyano-11β,17α-dihydroxyandrost-4-en-3-one (IA)

11β-Hydroxyandrost-4-en-3,17-dione (OA, 5 gms) is added to acetone cyanohydrin (10 ml) and methanol (20 ml). A saturated aqueous solution of potassium cyanide (5 ml) is added to the steroid mixture. The mixture is stirred for 2½ hours during which time the product precipitates. The precipitate is filtered, washed with buffer (pH 7, 25 ml) and water to give the title compound. This material is purified by chromatography on silica gel (20% ethyl acetate-chloroform). The appropriate fractions are pooled and concentrated to give a solid which is recrystallized from ethyl acetate to give the title compound, $[\alpha]_D^{20}+158°$ (DMSO); IR (KBr)=3500, 3250, 2830—3010, 2220, 1650, cm$^{-1}$; NMR (CDCl$_3$/CD$_3$OD, 1:1)=1.2, 1.47, 4.2, 4.4 and 5.6 δ

EXAMPLE 26

17β-Cyano-11β,17α-dihydroxyandrosta-1,4-dien-3-one (IB)

11β-Hydroxyandrosta-1,4-diene-3,17-dione (OB, 5 gms) is mixed with acetone cyanohydrin (10 ml) and methanol (10 ml). A saturated aqueous solution of potassium cyanide (10 ml) is added and after 5 minutes, a solution is obtained. The reaction mixture is stirred for one hour, during which time, the product is crystallized. A buffer (ph 7, 50 ml) is added and the slurry filtered. The crystals are washed with buffer, water and dried. The solid material is recrystallized from ethyl acetate to give the title compound $[\alpha]_D+90°$ (DMSO); IR (KBr)=3365, 3010, 2850, 2220, 1650, 1600, 1570; cm$^{-1}$; NMR (CDCl$_3$/CD$_3$OD, 1:1)=1.23, 1.50, 4.18, 4.4, 5.94, 6.18 and 7.33 δ

EXAMPLE 27

17β-Cyano-11β,17α-dihydroxy-6α-methylandrost-4-en-3-one (IA)

11β-Hydroxy-6α-methylandrost-4-ene-3,17-dione (OA, 0.51 gms) is treated with acetone cyanohydrin (1 ml) and methanol (1 ml) and saturated potassium cyanide (1 ml). After several hours, buffer (pH 7, 5 ml) is added and the precipitate filtered, washed with water and dried to give a solid. This material is slurried in glacial acetic acid, filtered, washed with acetic acid water and dried to give the title compound $[\alpha]_D+117°$ (DMSO); IR (KBr)=3410, 3080, 2840, 2225, 1655 and 1602; cm$^{-1}$; NMR (CDCl$_3$/CD$_3$OD, 1:1) 1.08, 1.22, 1.47, 4.33, 4.40 and 5.65 δ

EXAMPLE 28

17β-Cyano-11β,17α-dihydroxy-6α-methylandrosta-1,4-dien-3-one (IB)

11β-Hydroxy-6α-methylandrosta-1,4 -diene-3,17-dione (OB, 2.59 gms) is reacted with acetone cyanohydrin (5 ml), methanol (5 ml), and a saturated cyanide solution (5 ml). After three hours of mixing, the reaction is complete as measured by TLC (toluene/ethyl acetate: 20/80). The reaction mixture is diluted with buffer (pH 7, 20 ml), giving a solid which is filtered, washed with water, and dried to give the title compound $[\alpha]_D+85°$ (DMSO); IR (KBr) 3390, 3300, 3010, 2840, 2230, 1650, 1625, 1580, cm$^{-1}$; NMR (CDCl$_3$/CD$_3$OD, 1:1)=1.1, 1.22, 1.48, 4.40, 5.95, 6.2, and 7.30 δ

EXAMPLE 29

17β-Cyano-3β,11β,17α-trihydroxyandrosta-3,5-diene 3-methyl ether 17α-(α-ethoxyethyl)-ether (IIAa)

17β-Cyano-3β,11β,17α-trihydroxyandrosta-3,5-diene 3-methyl ether (IAa, Example 24, 343 ml) toluene (1 ml), methylene chloride (0.1 ml), ethyl vinyl ether (0.6 ml), and pyridine hydrochloride (12 mg) are heated overnight in a small pressure vessel at 85°. TLC (20% ethyl acetate-chloroform) shows the reaction to be complete, containing a less polar product. Triethylamine (0.3 ml), buffer (pH 7, 5 ml) and toluene (5 ml) are added and mixed. The layers are separated, the organic phase dried and organic solvents removed to give the title compound.

EXAMPLE 30

11$\beta$,17$\alpha$-Hydroxypregn-4-ene-3,20-dione (XXII)

17$\beta$-Cyano-3$\beta$,11$\beta$,17$\alpha$-trihydroxyandrosta-3,5-diene 3-methyl ether 17$\alpha$-($\alpha$-ethoxyethyl)-ether (IIAa, Example 29), methyl lithium (1.5N, 3 ml) are allowed to react at 20°–25° overnight. Water (3 ml), acetic acid (3 ml) and methanol (10 ml) are added. The reaction mixture is taken up in methylene chloride (50 ml) and washed with water (50 ml). The organic phase is separated and washed twice with sulfuric acid (2N, 25 ml) followed by water. The organic solvent is removed and replaced with a mixture of ethanol, concentrated hydrochloric acid and water and allowed to stand overnight. Methylene chloride is added, the mixture washed with water, the organic solvents removed, and the material crystallized from ethyl acetate to give a crystalline product which is identical with 11$\beta$,17$\alpha$-dihydroxyprogesterone.

EXAMPLE 31

17$\alpha$-($\alpha$-ethoxyethyl)-ether-20-trifluoroacetylaminopregn-5-ene 3-ethylidine ketal (IIIAb)

A solution of 17$\beta$-cyano-17$\alpha$-($\alpha$-ethoxyethyl)-etherandrost-5-ene-3-ethylidine ketal (IIAb, Example 4, 3.5 mmole) in toluene (12.5 ml) is cooled to 0°. Methyl lithium (1.6M, 2.95 ml) in diethyl ether is added (dropwise) over a period of 4 hours. The reaction is stirred an additional 3 hours at 0° and then quenched at −35° with pyridine (0.76 ml) and trifloroacetic hydride (1 ml). The reaction mixture is extracted 3 times with phosphate buffer (pH 7), the organic layer is dried over sodium sulfate and concentrated to give the title compound. NMR (CDCl$_3$) 0.71, 1.01, 1.20, 2.05, 2.11, 3.40, 3.90, 4.63 and 5.28 $\delta$

EXAMPLE 32

17$\alpha$-($\alpha$-ethoxyethyl)-ether-20-trifluoroacetylaminopregna-5,20-diene-3-ethylidine ketal (VAb)

DBU (50 micro liters, 0.3 mmole) is added to 17$\alpha$-($\alpha$-ethoxyethyl)-ether-20-trifluoroacetylaminopregna-5-ene-3-ethylidine ketal (IIIAb, Example 31, 3.5 mmole) in toluene (10 ml) and stirred at 20°–25° for 70 minutes. The mixture is then extracted 3 times with phosphate buffer (pH 7), dried over sodium sulfate and concentrated to an oil. NMR (CDCl$_3$) 0.70, 1.03, 1.23, 3.47, 3.90, 4.70, 5.04, 5.18, 5.29, 5.88 and 6.17 $\delta$

EXAMPLE 33

21-Bromo-17$\alpha$-($\alpha$-ethoxyethyl)-ether-20-trifluoroacetyliminopregn-5-en 3-ethylidine ketal (XVAb) and
21-Bromo-17$\alpha$-($\alpha$-ethoxyethyl)-ether-20-trifluoroacetylaminopregna-5,20-diene 3-ethylidine ketal (XXAb)

17$\alpha$-($\alpha$-ethoxyethyl)-ether-20-trifluoroacetylaminopregna-5,20-diene 3-ethylidine ketal (VAb, Example 32, 190 mg) is dissolved in methylene chloride (0.5 ml) and methanol (0.125) with triethylamine (61 micro liters) and water (20 micro liters). The mixture is cooled to 0°. Pyridinium hydrobromide perbromide (0.105 g) is added incrementally. The reaction mixture is stirred at 0° for 2-1/5 hours and then extracted with phosphate buffer (pH 7). The organic layer is dried over sodium sulfate and concentrated to give the title compounds. NMR (CDCl$_3$) 0.71, 0.75, 0.82, 1.03, 1.27, 3.43, 3.93, 4.33, 4.70, 5.3, 6.47 and 6.53 $\delta$

EXAMPLE 34

21-Bromo-17$\alpha$-hydroxyprogesterone (XIIIA) and
21-Bromo-17$\alpha$-trifluoroacetylprogesterone (XIA)

21-Bromo-17$\alpha$-($\alpha$-ethoxyethyl)-ether-20-trifluoroacetyliminopregn-5-en-3-ethylidine ketal (XVAb, Example 33) and 21-bromo-17$\alpha$-($\alpha$-ethoxyethyl)-ether-20-acetylaminopregna-5,20-diene-3-ethylidine ketal (XXAb, Example 33) as an oil (110 ml) containing a mixture of XVAb and XXAb is dissolved in THF (1.2 ml) with sulfuric acid (1N, 0.2 ml). The mixture is heated at 54° for 9 hours. The mixture is extracted into ethyl acetate, washed with phosphate buffer (pH 7) to neutrality. The mixture is then concentrated to an oil which as shown by NMR analysis contains the title compound.

EXAMPLE 35

21-Bromo-17$\alpha$-hydroxyprogesterone (XIIIA)

21-Bromo-17$\alpha$-hydroxyprogesterone (XIIIA, Example 34) and 21-bromo-17$\alpha$-trifluoroacetylprogesterone (XIA, Example 34) as an oil containing 160 mg of a mixture of XIIIA and XIA is dissolved in methanol (6.0 ml) and water (1 ml) with sodium bicarbonate (172 mg). The mixture is stirred at 20°–25° for 2 hours. The mixture is extracted with methylene chloride, the methylene chloride extract is concentrated to give the title compound. NMR (CDCl$_3$) 0.73, 1.20, 4.09, 4.37 and 5.69 $\delta$.

EXAMPLE 36

17R,2'-Methyl-4'-bromomethylenespiro-3-ethylenedioxyandrost-5-en-17,5'(4'H)-oxazole (XAb)

21-Bromo-17$\alpha$-($\alpha$-ethoxyethyl)-ether-20-acetyliminopregn-5-3-ethylidine ketal (XVAb, Example 15, 43 mg) is stirred in ethanol (1.5 ml) with boron trifluoride etherate (0.076 mM) at 20°–25° for 3 hr. The reaction is quenched with phosphate buffer (pH 7) and extracted into ethyl acetate. NMR and TLC confirmed the identity of the title compound.

EXAMPLE 37

17$\alpha$-($\alpha$-ethyoxyethyl)-ether-20-trimethylacetylaminopregna-5,20-diene 3-ethylidine ketal (VAb)

A 2:1 mixture of 17$\alpha$-($\alpha$-ethoxyethyl)-ether-20-trimethylacetylaminopregna-5,20-diene 3-ethylidine ketal (VAb) and 17$\alpha$($\alpha$-ethoxyethyl)-ether-20-trimethylacetyl-aminopregn-5-ene 3-ethylidine ketal (IIIAb) is dissolved in toluene (5 ml) and THF (1 ml) and stirred with several mg of magnesium bromide under nitrogen at 20°–25°. After 16 hr all of (IIIAb) is epimerized to (VAb).

EXAMPLE 38

21-Bromo-17α-hydroxyprogesterone 17-acetate (XIA)

21-Bromo-17α-(α-ethoxyethyl)-ether-20-acetylimino-pregn-5-ene 3-ethylidine ketal (XVAb), Example 15, 100 mg) is stirred in methanol and sulfuric acid (1N, 0.4 ml) for 19 hr at 20°–25° followed by 46° for 3 days giving the title compound.

EXAMPLE 39

21-Bromo-17α-hydroxyprogesterone 17-acetate (XIA)

21-Bromo-17α-(α-ethoxyethyl)-ether-20-acetylaminopregna-5,20-diene 3-ethylidine ketal (XXAb, 100 mg) is stirred in acetic acid (1 ml) and water (0.3 ml) at 60° for 18 hr to give the title compound.

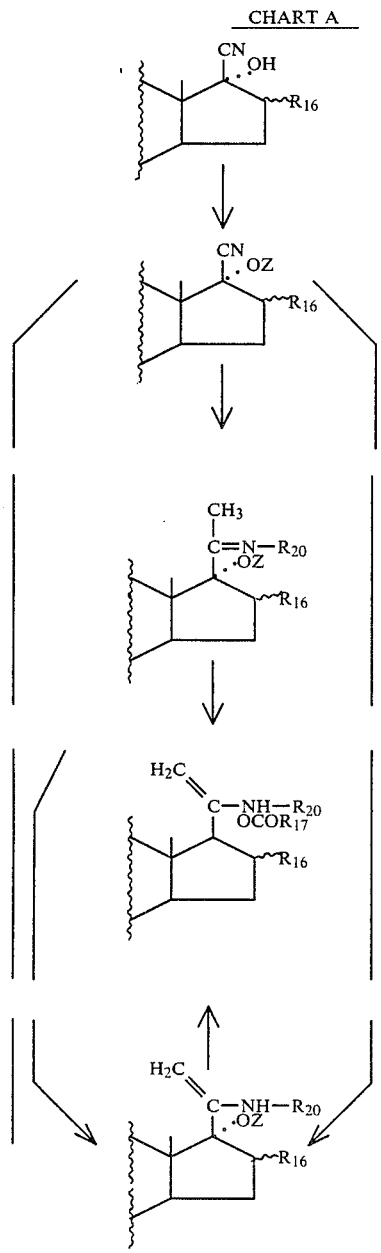

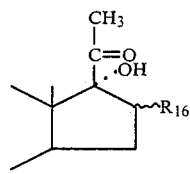

(XXII)

CHART B

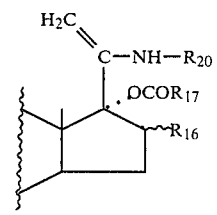

(IV)

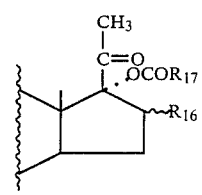

(VI)

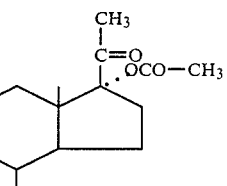

(VI'A)

(VII)

-continued
CHART B
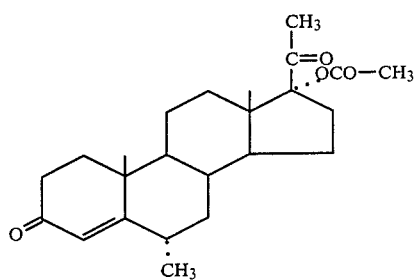
(VIII)
CHART C
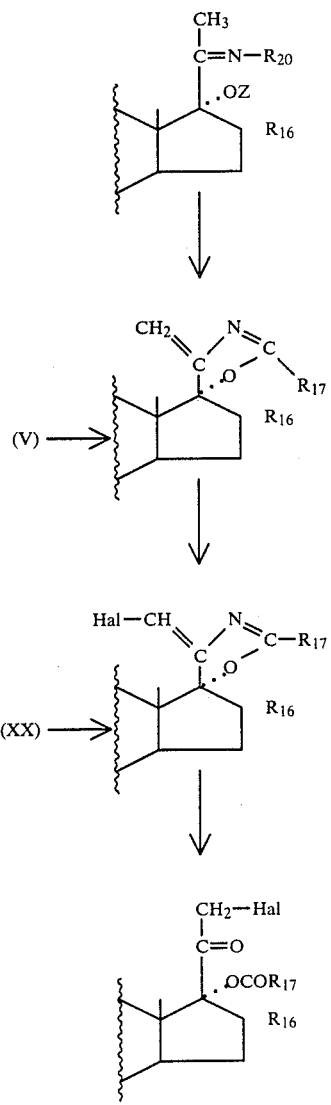
CHART D
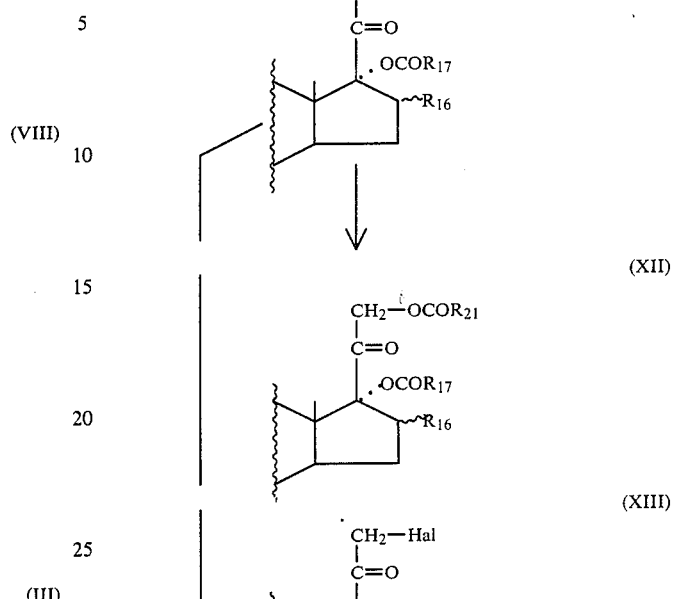
CHART E
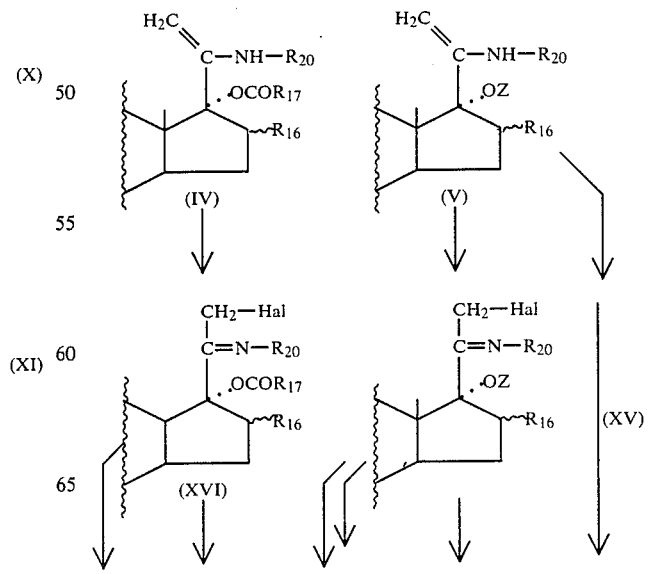

-continued
CHART E
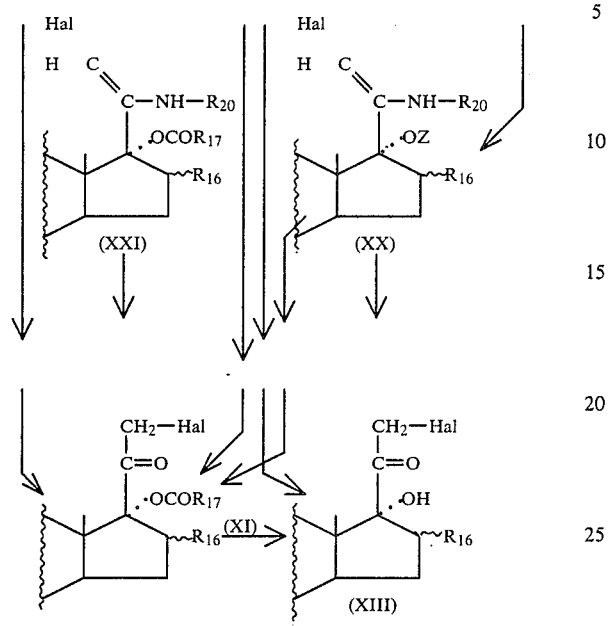
CHART F
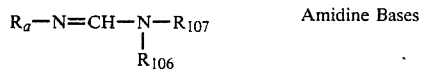
Amidine Bases
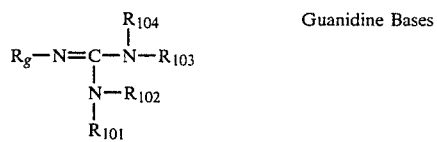
Guanidine Bases
CHART G
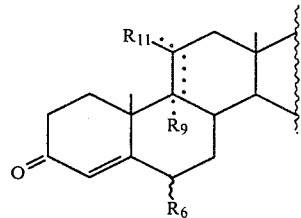
(A)
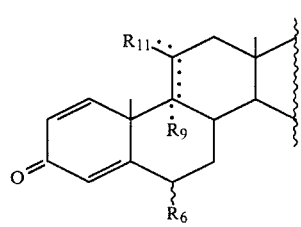
(B)
-continued
CHART G
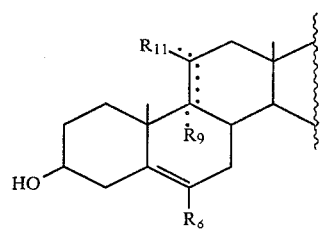
(C)
CHART H
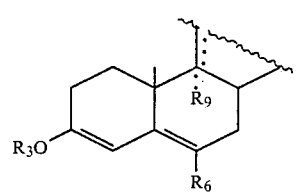
(Aa)
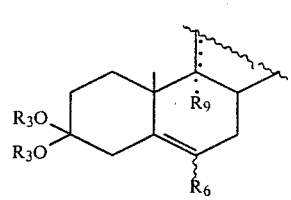
(Ab)
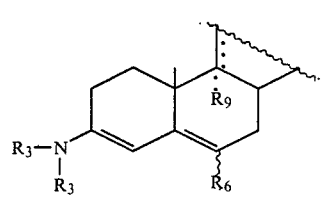
(Ac)
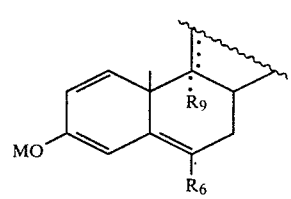
(Ba)
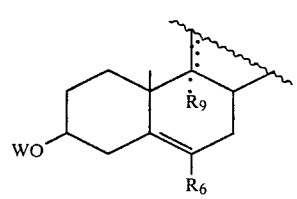
(Ca)
ENUMERATED EMBODIMENTS
The following Enumerated Embodiments further describe the applicant's invention.
1. A 17β-cyano-17α-hydroxy steroid of the formula

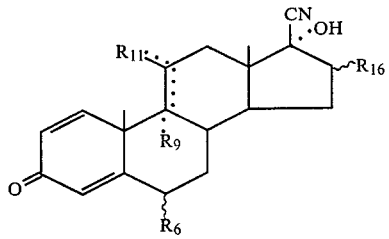

(IB)

and C$_3$ protected forms thereof where

R$_6$ is a hydrogen or fluorine atom or methyl group;

R$_9$ is nothing, a hydrogen, fluorine or oxygen atom which makes the C ring
 (a) $\Delta^{9(11)}$ when R$_9$ is nothing and
 (b) 9β,11-epoxide when R$_9$ is an oxygen atom;

R$_{11}$ is a hydrogen or oxygen atom, two hydrogen atoms, or α- or β-hydroxyl group which makes the C-ring
 (a) $\Delta^{9(11)}$ when R$_{11}$ is a hydrogen atom,
 (b) 9β,11β-epoxide when R$_{11}$ is an oxygen atom and .... between C$_{11}$ and R$_{11}$ is a single bond, and
 (c) a ketone when R$_{11}$ is an oxygen atom and .... between C$_{11}$ and R$_{11}$ is a double bond;

R$_{16}$ is a hydrogen atom or methyl group;

.... is a single or double bond; and

~ indicates that the attached atom or group can be in either the α or β configurations.

2. A 17β-cyano-17α-hydroxy steroid according to Enumerated Embodiment 1 where R$_9$ is nothing, R$_{11}$ is a hydrogen atom and the C-ring contains a $\Delta^{9(11)}$ double bond.

3. A 17β-cyano-17α-hydroxy steroid according to Enumerated Embodiment 1 which is seleted from the group consisting of 17β-cyano-11β,17α-dihydroxyandrosta-1,4-dien-3-one and 17β-cyano-11β,17α-dihydroxy-6α-methylandrosta-1,4-diene-3-one.

4. A 17-protected-17β-cyano-17α-hydroxy steroid of the formula

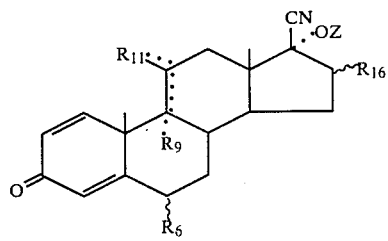

(II B)

and C$_3$ protected forms thereof where

R$_6$ is a hydrogen or fluorine atom or methyl group;

R$_9$ is nothing, a hydrogen, fluorine or oxygen atom which makes the C ring
 (a) $\Delta^{9(11)}$ when R$_9$ is nothing and
 (b) 9β,11-epoxide when R$_9$ is an oxygen atom;

R$_{11}$ is a hydrogen or oxygen atom, two hydrogen atoms, or α- or β-hydroxyl group which makes the C-ring
 (a) $\Delta^{9(11)}$ when R$_{11}$ is a hydrogen atom,
 (b) 9β,11β-epoxide when R$_{11}$ is an oxygen atom and .... between C$_{11}$ and R$_{11}$ is a single bond, and
 (c) a ketone when R$_{11}$ is an oxygen atom and .... between C$_{11}$ and R$_{11}$ is a double bond;

R$_{16}$ is a hydrogen atom or methyl group;

Z is selected from the group consisting of a TMS, THP, methoxymethyl, t-butyl-dimethyl silyl and EEE group;

.... is a single or double bond; and

~ indicates that the attached atom or group can be in either the α or β configurations.

5. A steroid selected from the group consisting of an enimide of the formula

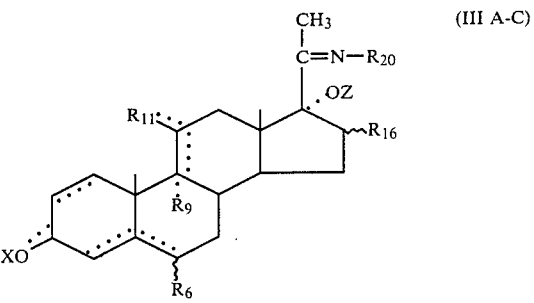

(III A-C)

an $\Delta^{20}$-enamide of the formula

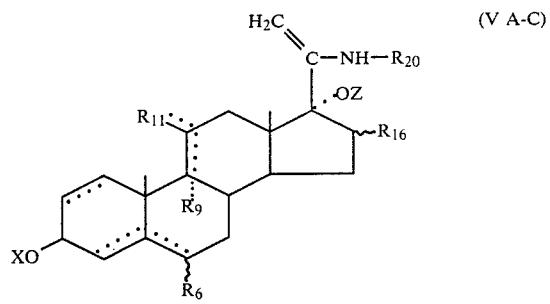

(V A-C)

and C$_3$ protected forms thereof where

R$_6$ is a hydrogen or fluorine atom or methyl group;

R$_9$ is nothing, a hydrogen, fluorine or oxygen atom which makes the C ring
 (a) $\Delta^{9(11)}$ when R$_9$ is nothing and
 (b) 9β,11-epoxide when R$_9$ is an oxygen atom;

R$_{11}$ is a hydrogen or oxygen atom, two hydrogen atoms, or α- or β-hydroxyl group which makes the C-ring
 (a) $\Delta^{9(11)}$ when R$_{11}$ is a hydrogen atom,
 (b) 9β,11β-epoxide when R$_{11}$ is an oxygen atom and .... between C$_{11}$ and R$_{11}$ is a single bond, and
 (c) a ketone when R$_{11}$ is an oxygen atom and .... between C$_{11}$ and R$_{11}$ is a double bond;

R$_{16}$ is a hydrogen atom or methyl group;

R$_{20}$ is —OC—R$_{20}'$ or —R$_{20}''$;

R$_{20}'$ is alkyl of 1 thru 5 carbon atoms, phenyl, phenyl substituted 0 thru 2 chlorine atoms, methyl or nitro groups;

R$_{20}''$ is —Si(CH$_3$)$_3$ or —Si(CH$_3$)$_2$C(CH$_3$)$_3$;

X refers to hydrogen atom or nothing;

Z is selected from the group consisting of a TMS, THP, methoxymethyl, t-butyl-dimethyl silyl and EEE group;

.... is a single or double bond; and

~ indicates that the attached atom or group can be in either the a or β configurations.

6. A steroid according to Enumerated Embodiment 5 where the $\Delta^4$-3-keto steroid (A) is protected as the

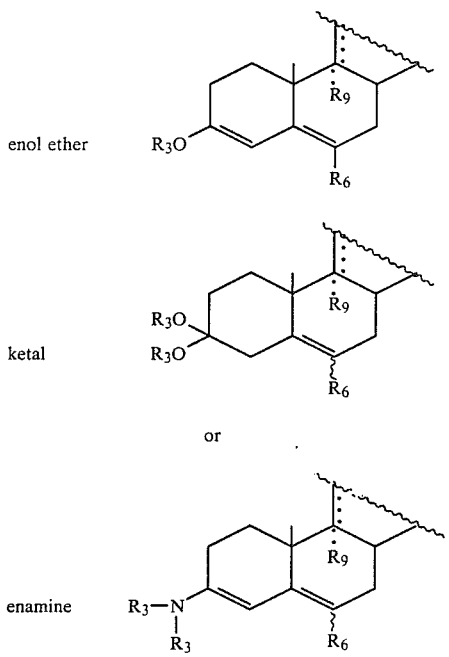

enol ether (Aa)

ketal (Ab)

or enamine (Ac)

where the $\Delta^{1,4}$-3-keto steroid (B) is protected as the

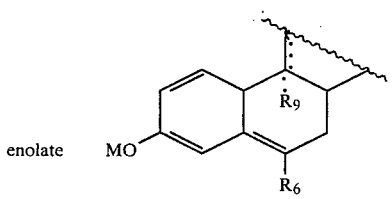

enolate (Ba)

and where the $3\beta$-hydroxy-$\Delta^5$ steroid (C) is protected as the

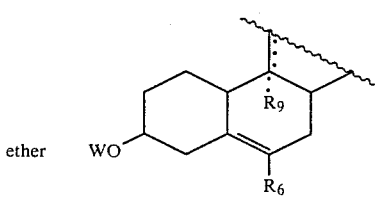

ether (Ca)

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

7. An enimide according to Enumerated Embodiment 5 where Z is selected from the group consisting of EEE, THP, TMS, and MEM.

8. An enimide according to Enumerated Embodiment 5 where $R_{20}$ is selected from the group consisting of acetyl, propionyl, benzoyl, formyl, trichloroacetyl, and trifluoroacetyl.

9. An enimide according to Enumerated Embodiment 5 which is selected from the group consisting of 17α-(α-ethoxyethyl)-ether-20-acetylaminopregn-5-en-3-ethylidine ketal, and 17α-(α-ethoxyethyl)-ether-20-trifluoroacetylamino-pregn-5-ene-3-ethylidine ketal.

10. A process for the preparation of a $C_3$ protected form of an enimide of the formula

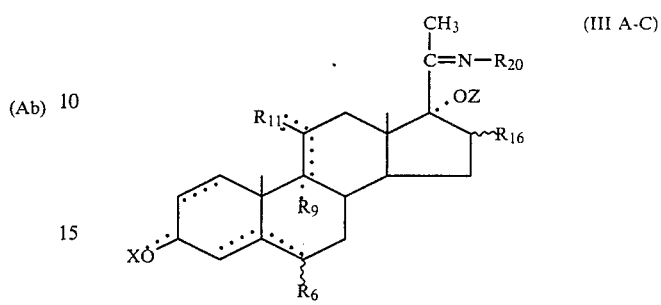

(III A-C)

which comprises (1) contacting a $C_3$ protected form of a 17-protected-17$\beta$-cyano-17α-hydroxy steroid of the formula

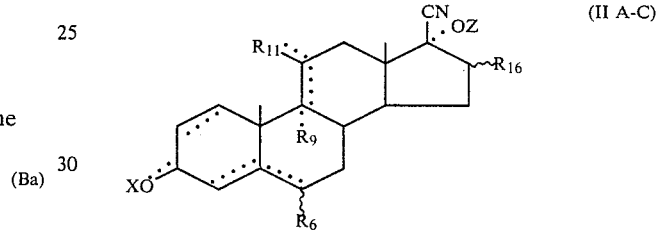

(II A-C)

with a methylating agent and (2) contacting the product of step (1) with an acylating or silating agent where $R_6$ is a hydrogen or fluorine atom or methyl group;

$R_9$ is nothing, a hydrogen, fluorine or oxygen atom which makes the C ring (a) $\Delta^{9(11)}$ when $R_9$ is nothing and (b) $9\beta$,11-epoxide when $R_9$ is an oxygen atom;

$R_{11}$ is a hydrogen or oxygen atom, two hydrogen atoms, or α- or $\beta$-hydroxyl group which makes the C-ring (a) $\Delta^{9(11)}$ when $R_{11}$ is a hydrogen atom, (b) $9\beta$,$11\beta$-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{16}$ is a hydrogen atom or methyl group;

$R_{20}$ is —OC—$R_{20}'$ or —$R_{20}''$;

$R_{20}'$ is alkyl of 1 thru 5 carbon atoms, phenyl, phenyl substituted 0 thru 2 chlorine atoms, methyl or nitro groups;

$R_{20}''$ is —Si(CH$_3$)$_3$ or —SI(CH$_3$)$_2$C(CH$_3$)$_3$;

X refers to a hydrogen atom or nothing;

Z is selected from the group consisting of a TMS, THP, methoxymethyl, t-butyl-dimethyl silyl and EEE group;

.... is a single or double bond; and

~ indicates that the attached atom or group can be in either the α or $\beta$ configurations.

11. A process according to Enumerated Embodiment 10 where the $\Delta^4$-3-keto steroid (A) is protected as the

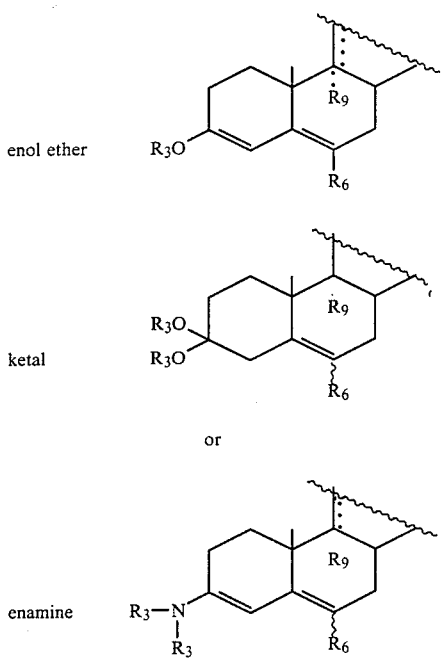

enol ether (Aa)

ketal (Ab)

or enamine (Ac)

where the $\Delta^{1,4}$-3-keto steroid (B) is protected as the

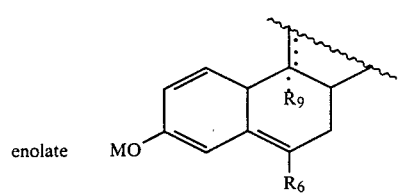

enolate (Ba)

and where the $3\beta$-hydroxy-$\Delta^5$ steroid (C) is protected as the

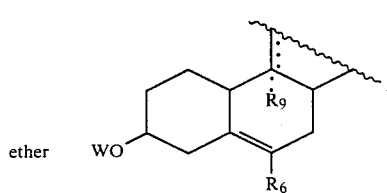

ether (Ca)

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is lithium, sodium, potassium, magnesium or calcium atom; and

W is a TMS, THP, or ethoxy ethyl group.

12. A process according to Enumerated Embodiment 10 where the methylating agent is selected from the group consisting of methyl lithium, methyl magnesium bromide, methyl magnesium chloride and methyl magnesium iodide.

13. A process according to Enumerated Embodiment 10 where the acylating or silating agent is selected from the group consisting of $(R_{20})_2O$, $R_{20}J$, or $R_{20}''J$ where $R_{20}''$ is $-Si(CH_3)_3$ or $-Si(CH_3)_2C(CH_3)_3$ and where J is a chlorine, bromine or iodine atom.

14. A process according to Enumerated Embodiment 13 where the acylating agent is acetic anhydride or acetyl chloride.

15. A process for the preparation of a $C_3$ protected form of a $\Delta^{20}$-enamide acylate of the formula

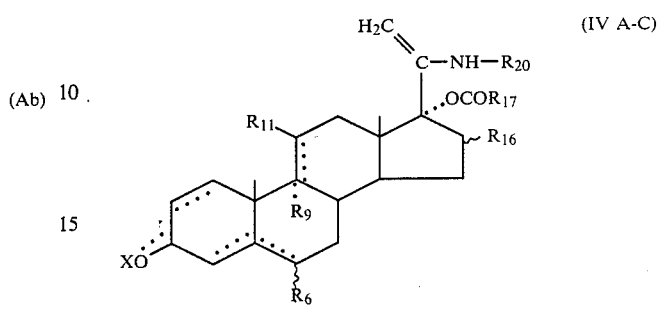 (IV A-C)

which comprises contacting a steroid selected from the group consisting of a $C_3$ protected form of an enimide of the formula

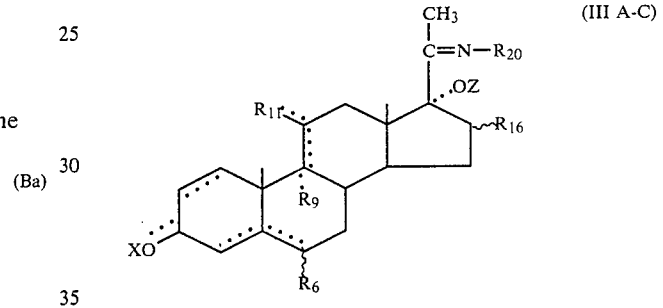 (III A-C)

or a $C_3$ protected form of a $\Delta^{22}$-enamide of the formula

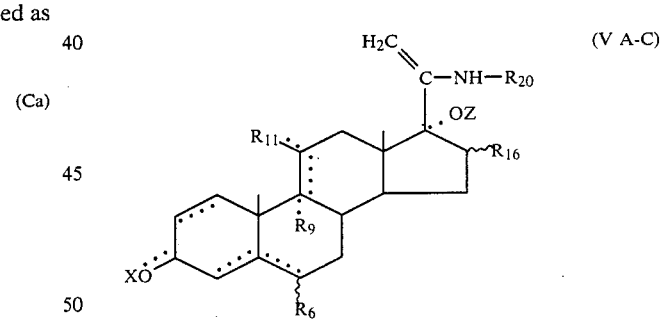 (V A-C)

with a carboxylic acid of the formula $R_{17}COOH$ and an anhydride of the formula $(R_{17}CO)_2O$ where $R_6$ is hydrogen or fluorine atom or methyl group;

$R_9$ is nothing, a hydrogen, fluorine or oxygen atom which makes the C ring (a) $\Delta^{9(11)}$ when $R_9$ is nothing and (b) $9\beta,11$-epoxide when $R_9$ is an oxygen atom;

$R_{11}$ is a hydrogen or oxygen atom, two hydrogen atoms, or $\alpha$- or $\beta$-hydroxyl group which makes the C-ring (a) $\Delta^{9(11)}$ when $R_{11}$ is a hydrogen atom, (b) $9\beta,11\beta$-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{16}$ is a hydrogen atom or methyl group;

$R_{17}$ is a hydrogen atom alkyl of 1 thru 5 carbon atoms, phenyl substituted with zero thru 2 chlorine, trichloromethyl, trifluoromethyl;

$R_{20}$ is —OC—$R_{20}'$ or —$R_{20}''$;

$R_{20}'$ is alkyl of 1 thru 5 carbon atoms, phenyl, phenyl substituted 0 thru 2 chlorine atoms, methyl or nitro groups;

$R_{20}''$ is —Si(CH$_3$)$_3$ or —SI(CH$_3$)$_2$C(CH$_3$)$_3$;

Z is selected from the group consisting of a TMS, THP, methoxymethyl, t-butyl-dimethyl silyl and EEE group;

X refers to a hydrogen atom or nothing;

.... is a single or double bond; and

~ indicates that the attached atom or group can be in either the a or β configurations.

16. A process according to Enumerated Embodiment 15 where the Δ$^4$-3-keto steroid (A) is protected as the

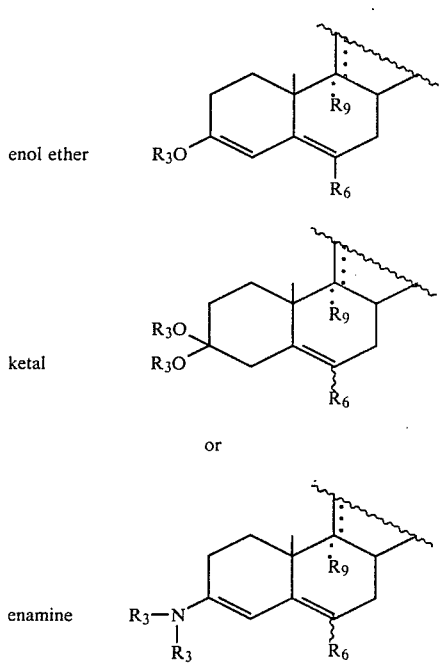

where the Δ$^{1,4}$-3-keto steroid (B) is protected as the

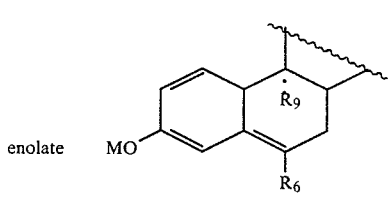

and where the 3β-hydroxy-Δ$^5$ steroid (C) is protected as the

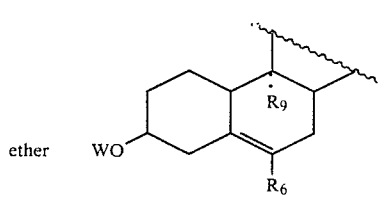

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

17. A process according to Enumerated Embodiment 15 where $R_{17}$ is methyl, ethyl or phenyl.

18. A process for the preparation of a C$_3$ protected form of a Δ$^{20}$-enamide of the formula

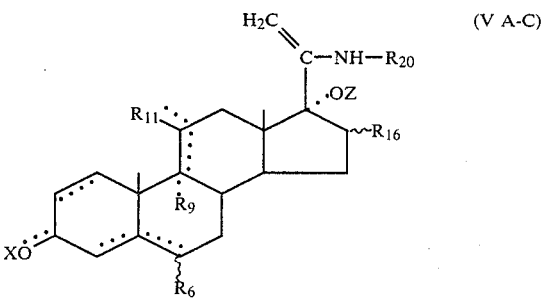

which comprises contacting a C$_3$-protected form of an enimide of the formula

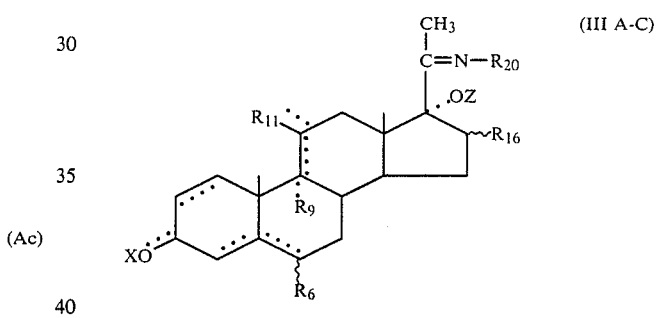

with an acid or base where $R_6$ is a hydrogen or fluorine atom or methyl group;

$R_9$ is nothing, a hydrogen, fluorine or oxygen atom which makes the C ring (a) Δ$^{9(11)}$ when $R_9$ is nothing and (b) 9β,11-epoxide when $R_9$ is an oxygen atom;

$R_{11}$ is a hydrogen or oxygen atom, two hydrogen atoms, or α- or β-hydroxyl group which makes the C-ring (a) Δ$^{9(11)}$ when $R_{11}$ is a hydrogen atom, (b) 9β,11β-epoxide when $R_{11}$ is an oxygen atom and .... between C$_{11}$ and $R_{11}$ is a single bond, and (c) a ketone when $R_{11}$ is an oxygen atom and .... between C$_{11}$ and $R_{11}$ is a double bond;

$R_{16}$ is a hydrogen atom or methyl group;

$R_{20}$ is —OC—$R_{20}'$ or —$R_{20}''$;

$R_{20}'$ is alkyl of 1 thru 5 carbon atoms, phenyl, phenyl substituted 0 thru 2 chlorine atoms, methyl or nitro groups;

$R_{20}''$ is —Si(CH$_3$)$_3$ or —SI(CH$_3$)$_2$C(CH$_3$)$_3$;

X refers to a hydrogen atom or nothing;

Z is selected from the group consisting of a TMS, THP, methoxymethyl, t-butyl-dimethyl silyl and EEE group;

.... is a single or double bond; and

~ indicates that the attached atom or group can be in either the a or β configurations.

19. A process according to Enumerated Embodiment 18 where the $\Delta^4$-3-keto steroid (A) is protected as the

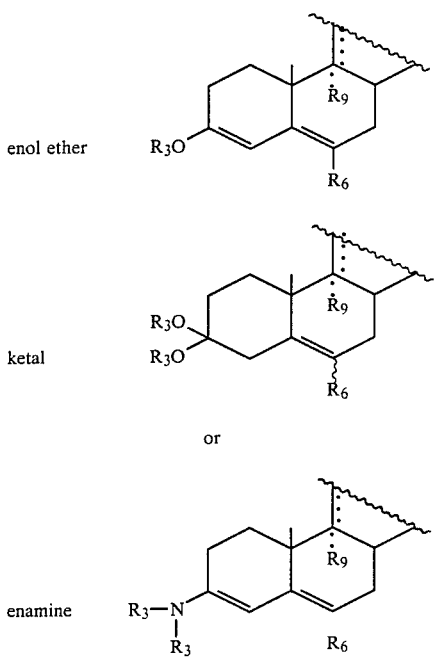

where the $\Delta^{1,4}$-3-keto steroid (B) is protected as the

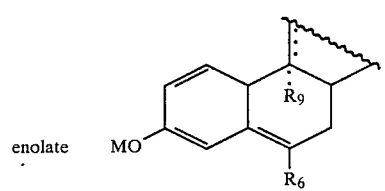

and where the $3\beta$-hydroxy-$\Delta^5$ steroid (C) is protected as the

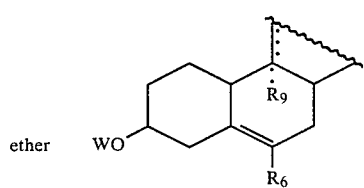

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

20. A process according to Enumerated Embodiment 18 where the acid is a Lewis acid or carboxylic acid.

21. A process according to Enumerated Embodiment 20 where the acid is selected from the group consisting of acetic, propionic, benzoic or citric acid.

22. A process according to Enumerated Embodiment 18 where the base is selected from the group consisting of DBU, DBN, amidine bases of the formula

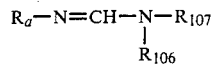

and quanidine bases of the formula

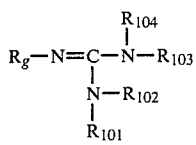

where $R_a$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine;

$R_g$ is $R_a$, a hydrogen atom or phenyl;

$R_{101}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine;

$R_{102}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine;

$R_{103}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine;

$R_{104}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a cyclic secondary amine selected from the group consisting of piperidine, pyrrolidine and morpholine;

$R_{106}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a secondary amine selected from the group consisting of piperidine, pyrrolidine or morpholine with the proviso that $R_{106}$ and $R_{107}$ combined cannot have more than 14 carbon atoms; $R_{106}$ and $R_{107}$ can be combined to form a secondary cyclic amine selected from the group consisting of piperidine, pyrrolidine and morpholine;

$R_{107}$ is alkyl of 1 thru 7 carbon atoms, cycloalkyl of 5 thru 7 carbon atoms, phenyl substituted with 1 thru 3 —$R_{100}$, —$OR_{105}$ or —$N(R_{105})_2$ where with the amine the $R_{105}$'s can be the same or different and can be combined to form a secondary amine selected from the group consisting of piperidine, pyrrolidine or morpholine with the proviso that $R_{106}$ and $R_{107}$ combined cannot have more than 14 carbon atoms; $R_{106}$ and $R_{107}$ can be combined to form a secondary cyclic amine selected from the group consisting of piperidine, pyrrolidine and morpholine.

23. A steroid selected from the group consisting of a 21-haloenimide of the formula

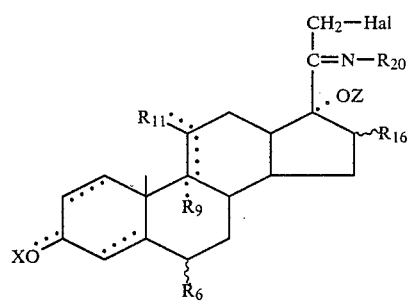
(XV A-C)

and a 21-halo-$\Delta^{20}$-enamide of the formula

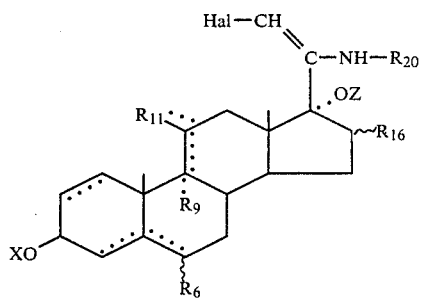
(XX A-C)

and $C_3$ protected forms thereof where $R_6$ is a hydrogen or fluorine atom or methyl group;

$R_9$ is nothing, a hydrogen, fluorine or oxygen atom which makes the C ring
 (a) $\Delta^{9(11)}$ when $R_9$ is nothing and
 (b) $9\beta,11$-epoxide when $R_9$ is an oxygen atom;

$R_{11}$ is a hydrogen or oxygen atom, two hydrogen atoms, or $\alpha$- or $\beta$-hydroxyl group which makes the C-ring
 (a) $\Delta^{9(11)}$ when $R_{11}$ is a hydrogen atom,
 (b) $9\beta,11\beta$-epoxide when $R_{11}$ is an oxygen atom and .... between $C_{11}$ and $R_{11}$ is a single bond, and
 (c) a ketone when $R_{11}$ is an oxygen atom and .... between $C_{11}$ and $R_{11}$ is a double bond;

$R_{16}$ is a hydrogen atom or methyl group;

$R_{20}$ is —OC—$R_{20}'$ or —$R_{20}''$;

$R_{20}'$ is alkyl of 1 thru 5 carbon atoms, phenyl, phenyl substituted 0 thru 2 chlorine atoms, methyl or nitro groups;

$R_{20}''$ is —Si(CH$_3$)$_3$ or —SI(CH$_3$)$_2$C(CH$_3$)$_3$;

X refers to a hydrogen atom or nothing;

Z is selected from the group consisting of a TMS, THP, methoxymethyl, t-butyl-dimethyl silyl and EEE group;

.... is a single or double bond;

~ indicates that the attached atom or group can be in either the $\alpha$ or $\beta$ configurations; and Hal is a chlorine, bromine, iodine, atom.

24. A steroid according to Enumerated Embodiment 23 where the $\Delta^4$-3-keto steroid (A) is protected as the

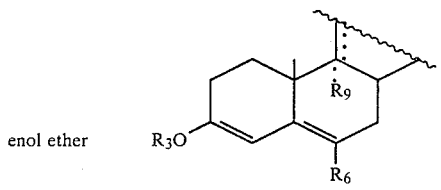
enol ether (Aa)

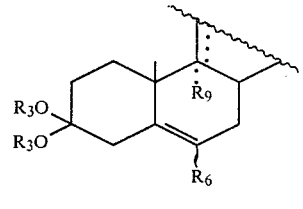
ketal (Ab)

or

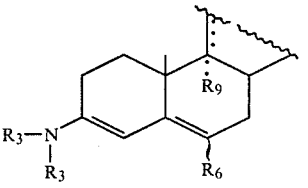
enamine (Ac)

where the $\Delta^{1,4}$-3-keto steroid (B) is protected as the

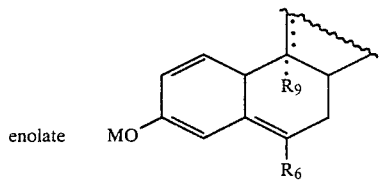
enolate (Ba)

and where the $3\beta$-hydroxy-$\Delta^5$ steroid (C) is protected as the

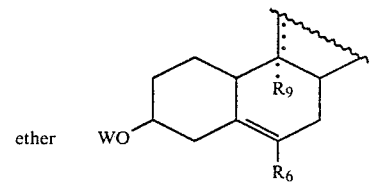
ether (Ca)

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

25. A steroid according to Enumerated Embodiment 23 where $R_9$ is nothing, $R_{11}$ is a hydrogen atom and the C-ring contains a $\Delta^{9,11}$ double bond.

26. A steroid according to Enumerated Embodiment 23 where Z is selected from the group consisting of EEE, THP, TMS, and MEM.

27. A steroid according to Enumerated Embodiment 23 where $R_{20}$ is selected from the group consisting of acetyl, propionyl, benzoyl, formyl, trichloroacetyl and trifluoroacetyl.

28. A steroid according to Enumerated Embodiment 23 where Hal is a bromine atom.

29. A steroid according to Enumerated Embodiment 23 which is selected from the group consisting of 21-bromo-17α-(α-ethoxyethyl)-ether-20-acetylamino-pregna-5-en-3-ethylidine ketal and 21-bromo-17α-(α-ethoxyethyl)-ether-20-acetylamino-pregna-5,20-diene-3-ethylidine ketal.

30. A process for the preparation of a $C_3$ protected form of an oxazoline of the formula

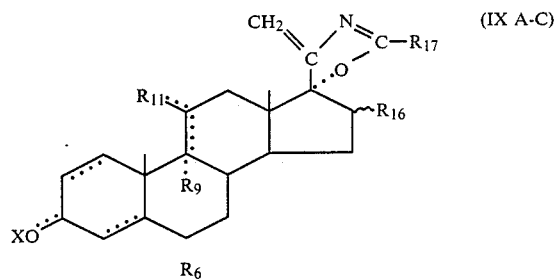
(IX A-C)

which comprises contacting a steroid selected from the group consisting of a $C_3$ protected form of an enimide of the formula

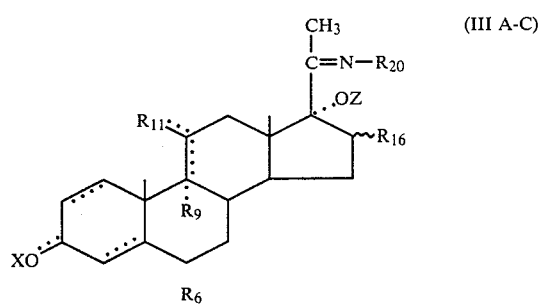
(III A-C)

or a $C_3$ protected form of a $\Delta^{20}$-enamide of the formula

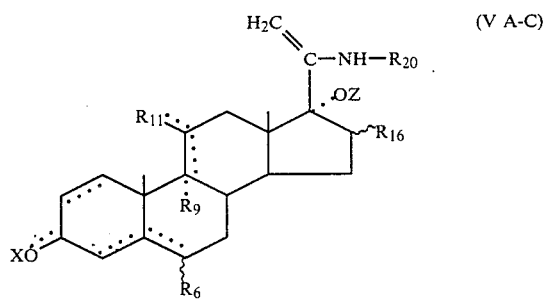
(V A-C)

with an acid in an organic solvent or mixtures thereof where $R_6$ is a hydrogen or fluorine atom or methyl group;

$R_9$ is nothing, a hydrogen, fluorine or oxygen atom which makes the C ring (a) $\Delta^{9(11)}$ when $R_9$ is nothing and (b) 9β,11-epoxide when $R_9$ is an oxygen atom;

$R_{11}$ is a hydrogen or oxygen atom, two hydrogen atoms, or α- or β-hydroxyl group which makes the C-ring (a) $\Delta^{9(11)}$ when $R_{11}$ is a hydrogen atom, (b) 9β,11β-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{16}$ is a hydrogen atom or methyl group;

$R_{17}$ is a hydrogen atom alkyl of 1 thru 5 carbon atoms, phenyl substituted with zero thru 2 chlorine, trichloromethyl, trifluoromethyl;

$R_{20}$ is $-OC-R_{20}'$ or $-R_{20}''$;

$R_{20}'$ is alkyl of 1 thru 5 carbon atoms, phenyl, phenyl substituted 0 thru 2 chlorine atoms, methyl or nitro groups;

$R_{20}''$ is $-Si(CH_3)_3$ or $-SI(CH_3)_2C(CH_3)_3$;

X refers to a hydrogen atom or nothing;

Z is selected from the group consisting of a TMS, THP, methoxymethyl, t-butyl-dimethyl silyl and EEE group;

.... is a single or double bond; and

~ indicates that the attached atom or group can be in either the α or β configurations.

31. A process according to Enumerated Embodiment 30 where the $\Delta^4$-3-keto steroid (A) is protected as the

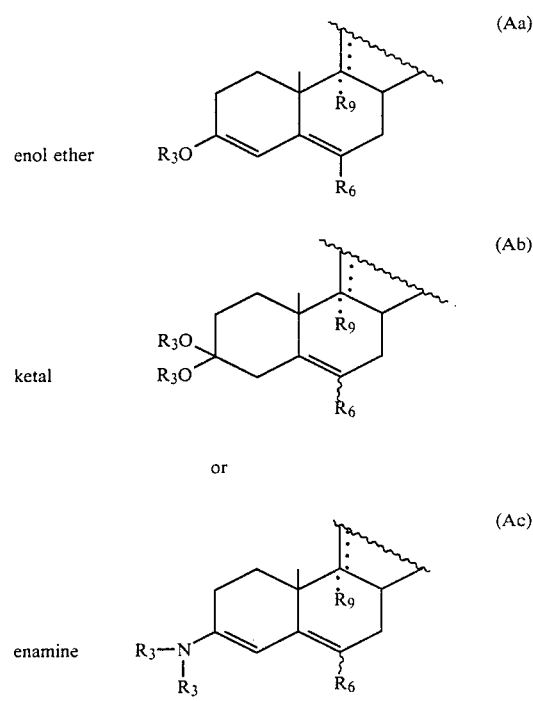

enol ether (Aa)

ketal (Ab)

or enamine (Ac)

where the $\Delta^{1,4}$-3-keto steroid (B) is protected as the

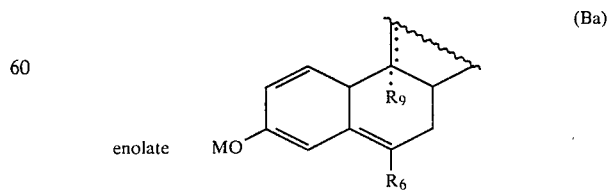

enolate (Ba)

and where the 3β-hydroxy-$\Delta^5$ steroid (C) is protected as the

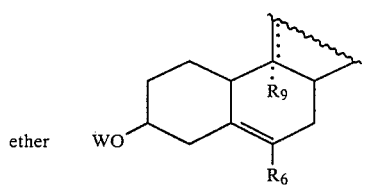

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

32. A process according to Enumerated Embodiment 30 where the acid is selected from the group consisting of mineral inorganic acids, organic acids and Lewis acids.

33. A process according to Enumerated Embodiment 32 where the acid is selected from the group consisting of p-TSA, acetic, sulfuric, hydrochloric, phosphoric, formic and benzoic.

34. A process for the preparation of a steroid selected from the group consisting of a $C_3$ protected form of a 21-halo enimide of the formula

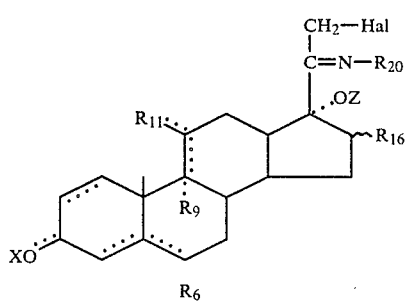

and a $C_3$ protected form of a 21-halo-$\Delta^{20}$-enamide of the formula

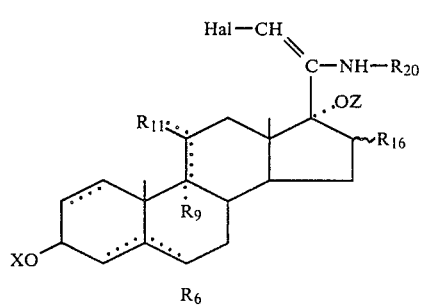

which comprises contacting a $C_3$ protected form of a $\Delta^{20}$-enamide of the formula

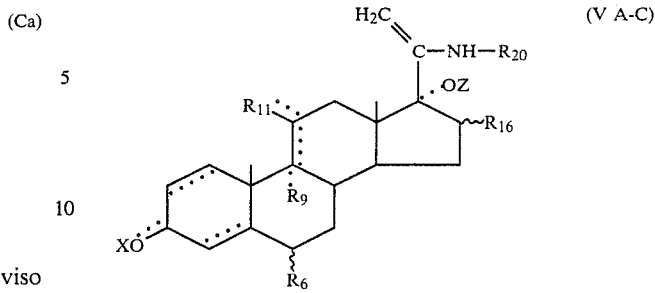

with a halogenating agent where $R_6$ is a hydrogen or fluorine atom or methyl group;

$R_9$ is nothing, a hydrogen, fluorine or oxygen atom which makes the C ring (a) $\Delta^{9(11)}$ when $R_9$ is nothing and (b) $9\beta,11$-epoxide when $R_9$ is an oxygen atom;

$R_{11}$ is a hydrogen or oxygen atom, two hydrogen atoms, or $\alpha$- or $\beta$-hydroxyl group which makes the C-ring (a) $\Delta^{9(11)}$ when $R_{11}$ is a hydrogen atom, (b) $9\beta,11\beta$-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{16}$ is a hydrogen atom or methyl group;

$R_{20}$ is —OC—$R_{20}'$ or —$R_{20}''$;

$R_{20}'$ is alkyl of 1 thru 5 carbon atoms, phenyl, phenyl substituted 0 thru 2 chlorine atoms, methyl or nitro groups;

$R_{20}''$ is —Si(CH$_3$)$_3$ or —SI(CH$_3$)$_2$C(CH$_3$)$_3$;

Z is selected from the group consisting of a TMS, THP, methoxymethyl, t-butyl-dimethyl silyl and EEE group;

X refers to a hydrogen atom or nothing;

.... is a single or double bond;

$\sim$ indicates that the attached atom or group can be in either the $\alpha$ or $\beta$ configurations; and Hal is a chlorine, bromine, iodine, atom.

35. A process according to Enumerated Embodiment 34 where the $\Delta^4$-3-keto steroid (A) is protected as the

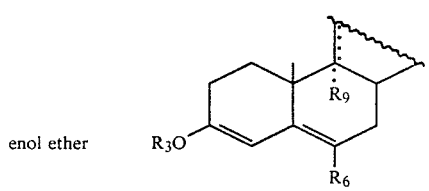

enol ether

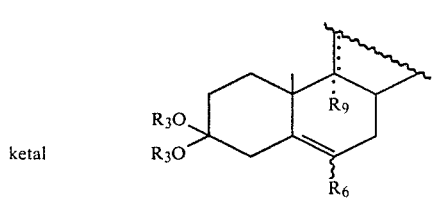

ketal or

-continued enamine 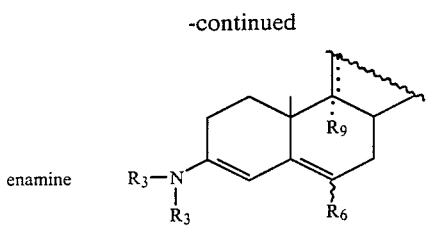 (Ac)

where the $\Delta^{1,4}$-3-keto steroid (B) is protected as the enolate 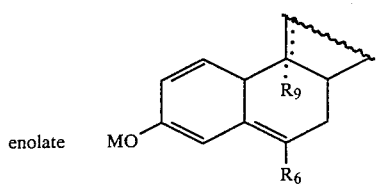 (Ba)

and where the $3\beta$-hydroxy-$\Delta^5$ steroid (C) is protected as the ether 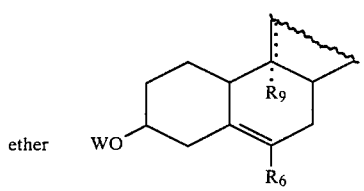 (Ca)

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

36. A process according to Enumerated Embodiment 34 where the halogenating agent is selected from the group consisting of bromine, NBS, NCS, dibromatin, pyridine hydrobromide.

37. A process for preparing a $C_3$ protected form of a 17α-hydroxy steroid of the formula

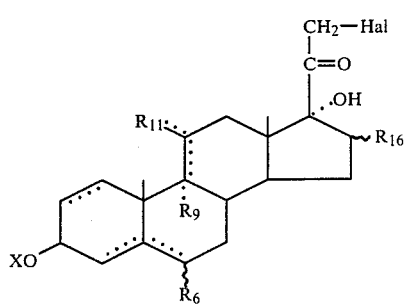 (XIII A-C)

which comprises (1) contacting a steroid selected from the group consisting of a $C_3$ protected form of a 21-halo enimide of the formula

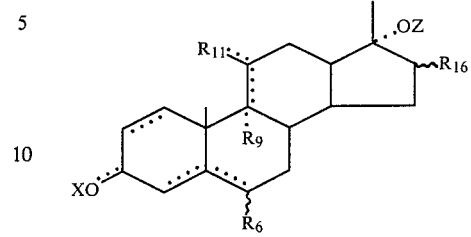 (XV A-C)

or a $C_3$ protected 21-halo-$\Delta^{20}$-enamide of the formula

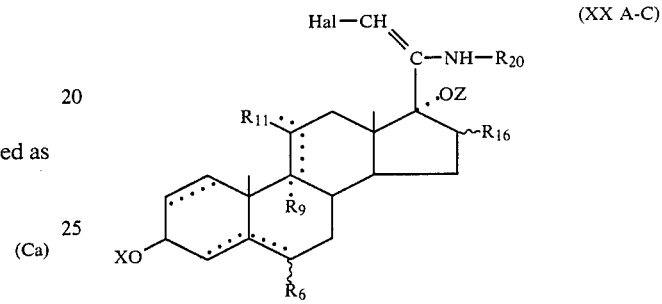 (XX A-C)

with an (aqueous) acid where $R_6$ is a hydrogen or fluorine atom or methyl group;

$R^9$ is nothing, a hydrogen, fluorine or oxygen atom which makes the C ring (a) $\Delta^{9(11)}$ when $R_9$ is nothing and (b) $9\beta,11$-epoxide when $R_9$ is an oxygen atom;

$R_{11}$ is a hydrogen or oxygen atom, two hydrogen atoms, or α- or β-hydroxyl group which makes the C-ring (a) $\Delta^{9(11)}$ when $R_{11}$ is a hydrogen atom, (b) $9\beta,11\beta$-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{16}$ is a hydrogen atom or methyl group;

$R_{20}$ is $-OC-R_{20}'$ or $-R_{20}''$;

$R_{20}'$ is alkyl of 1 thru 5 carbon atoms, phenyl, phenyl substituted 0 thru 2 chlorine atoms, methyl or nitro groups;

$R_{20}''$ is $-Si(CH_3)_3$ or $-SI(CH_3)_2C(CH_3)_3$;

X refers to a hydrogen atom or nothing;

Z is selected from the group consisting of a TMS, THP, methoxymethyl, t-butyl-dimethyl silyl and EEE group;

Hal is a chlorine, bromine, iodine, atom;

.... is a single or double bond; and

~ indicates that the attached atom or group can be in either the α or β configurations.

38. A process according to Enumerated Embodiment 37 where the $\Delta^4$-3-keto steroid (A) is protected as the enol ether 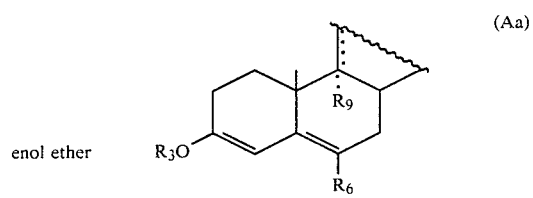 (Aa)

-continued ketal 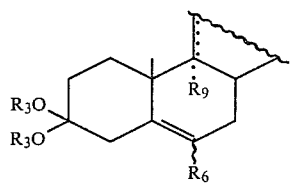 (Ab)

or enamine 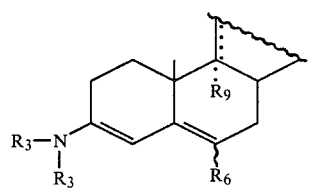 (Ac)

where the $\Delta^{1,4}$-3-keto steroid (B) is protected as the enolate 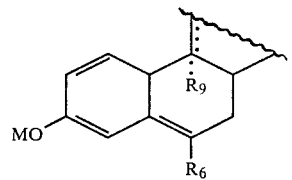 (Ba)

and where the $3\beta$-hydroxy-$\Delta^5$ steroid (C) is protected as the ether 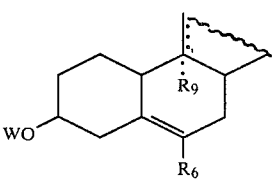 (Ca)

where $R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

39. A process according to Enumerated Embodiment 37 where the acid is an inorganic mineral acid.

40. A process according to Enumerated Embodiment 37 where the acid is sulfuric acid and the solvent is THF.

41. A $\Delta^{20}$-enamide acylate of the formula

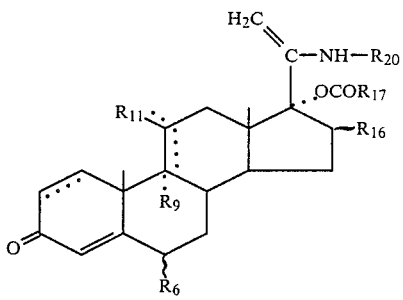 (IV A,B)

and $C_3$ protected forms thereof where $R_6$ is a hydrogen or fluorine atom or methyl group;

$R_9$ is nothing, a hydrogen, fluorine or oxygen atom which makes the C ring (a) $\Delta^{9(11)}$ when $R_9$ is nothing and (b) $9\beta,11$-epoxide when $R_9$ is an oxygen atom;

$R_{11}$ is a hydrogen or oxygen atom, two hydrogen atoms, or $\alpha$- or $\beta$-hydroxyl group which makes the C-ring (a) $\Delta^{9(11)}$ when $R_{11}$ is a hydrogen atom, (b) $9\beta,11\beta$-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{16}$ is a hydrogen atom or methyl group;

$R_{17}$ is a hydrogen atom alkyl of 1 thru 5 carbon atoms, phenyl substituted with zero thru 2 chlorine, trichloromethyl, trifluoromethyl;

$R_{20}$ is —OC—$R_{20}'$ or —$R_{20}''$;

$R_{20}'$ is alkyl of 1 thru 5 carbon atoms, phenyl, phenyl substituted 0 thru 2 chlorine atoms, methyl or nitro groups;

$R_{20}''$ is —Si(CH$_3$)$_3$ or —SI(CH$_3$)$_2$C(CH$_3$)$_3$;

.... is a single or double bond; and

~ indicates that the attached atom or group can be in either the a or $\beta$ configurations.

42. A $\Delta^{20}$-enamide acylate according to Enumerated Embodiment 41 where the $\Delta^4$-3-keto steroid (A) is protected as the enol ether 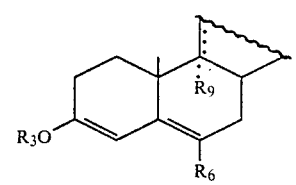 (Aa)

ketal 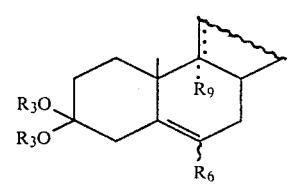 (Ab)

or

-continued

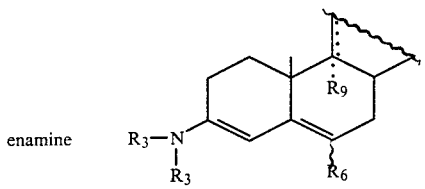

enamine and where the $\Delta^{1,4}$-3-keto steroid (B) is protected as the

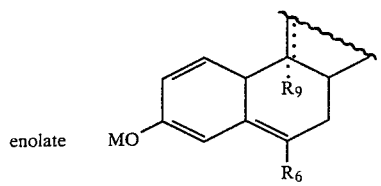

enolate where $R_3$ is alkyl of 1 thru 5 carbon atoms with the proviso that for the ketal (Ab) and the enamine (Ac), the $R_3$ groups can be connected and when connected may be connected by an oxygen or nitrogen atom; and M is a lithium, sodium, potassium, magnesium or calcium atom.

43. A $\Delta^{20}$-enamide acylate according to Enumerated Embodiment 41 where $R_9$ is nothing, $R_{11}$ is a hydrogen atom and the C-ring contains a $\Delta^{9,11}$ double bond.

44. A $\Delta^{20}$-enamide acylate according to Enumerated Embodiment 41 where $R_{20}$ is selected from the group consisting of acetyl, propionyl, benzoyl, formyl, trichloroacetyl and trifluoroacetyl.

45. A $\Delta^{20}$-enamide acylate according to Enumerated Embodiment 41 where $R_{17}$ is selected from the group consisting of methyl, ethyl and phenyl.

46. A $\Delta^{20}$-enamide acylate according to Enumerated Embodiment 41 which is 17α-acetoxy-20-acetylamino-pregna-5,20-dien-3-ethylidine ketal.

47. A 17β-cyano-17α-hydroxy steroid of the formula

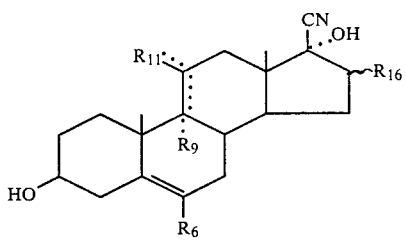

and $C_3$ protected forms thereof where $R_6$ is a hydrogen or fluorine atom or methyl group;

$R_9$ is nothing, a hydrogen, fluorine or oxygen atom which makes the C ring
  (a) $\Delta^{9(11)}$ when $R_9$ is nothing and
  (b) 9β,11-epoxide when $R_9$ is an oxygen atom;

$R_{11}$ is a hydrogen or oxygen atom, two hydrogen atoms, or α- or β-hydroxyl group which makes the C-ring
  (a) $\Delta^{9(11)}$ when $R_{11}$ is a hydrogen atom,
  (b) 9β,11β-epoxide when $R_{11}$ is an oxygen atom and .... between $C_{11}$ and $R_{11}$ is a single bond, and (c) a ketone when $R_{11}$ is an oxygen atom and .... between $C_{11}$ and $R_{11}$ is a double bond;

$R_{16}$ is a hydrogen atom or methyl group;

.... is a single or double bond; and

~ indicates that the attached atom or group can be in either the a or β configurations.

48. A 17β-cyano-17α-hydroxy steroid according to Enumerated Embodiment 47 where $R_9$ is nothing, $R_{11}$ is hydrogen atom and the C-ring contains a $\Delta^{9(11)}$ double bond.

49. A 17β-cyano-17α-hydroxy steroid of the formula

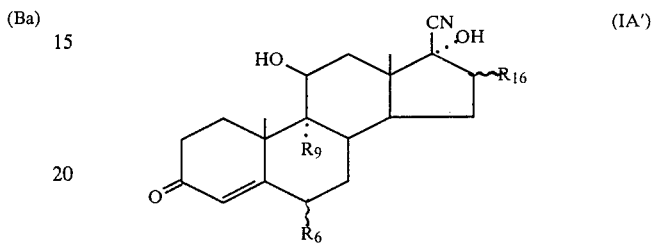

and $C_3$ protected forms thereof where $R_6$ is a hydrogen or fluorine atom or methyl group;

$R_9$ is nothing, a hydrogen, fluorine or oxygen atom which makes the C ring
  (a) $\Delta^{9(11)}$ when $R_9$ is nothing and
  (b) 9β,11-epoxide when $R_9$ is an oxygen atom;

$R_{16}$ is a hydrogen atom or methyl group; and

~ indicates that the attached atom or group can be in either the a or β configurations.

50. A 17β-cyano-17α-hydroxy steroid according to Enumerated Embodiment 49 which is selected from the group consisting of 17β-cyano-11β,∫α-dihydroxy-androst-4-en-3-one and 17β-cyano-11β,17α-dihydroxy-6-methylandrost-4-en-3-one.

I claim:

1. A 17β-cyano-17α-hydroxy steroid of the formula

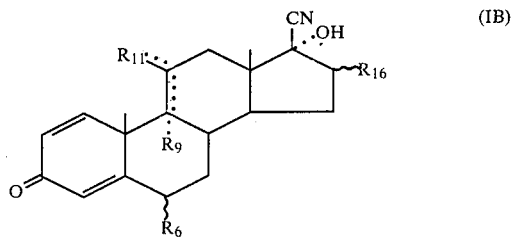

and its $C_3$ protected enolate

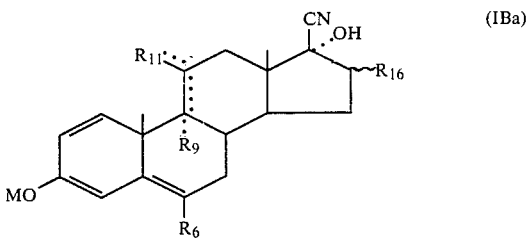

where $R_6$ is a hydrogen or fluorine atom, methyl or methylene group;

$R_9$ is nothing, a hydrogen, fluorine or oxygen atom, which makes the C-ring (a) $\Delta^{9(11)}$ when $R_9$ is nothing and
(b) $9\beta,11\beta$-epoxide when $R_9$ is an oxygen atom;

$R_{11}$ is a hydrogen or oxygen atom, two hydrogen atoms, or $\alpha$- or $\beta$-hydroxyl group which makes the C-ring
 (a) $\Delta^{9(11)}$ when $R_{11}$ is a hydrogen atom,
 (b) $9\beta,11\beta$-epoxide when $R_{11}$ is an oxygen atom and .... between $C_{11}$ and $R_{11}$ is a single bond, and
 (c) a ketone when $R_{11}$ is an oxygen atom and .... between $C_{11}$ and $R_{11}$ is a double bond;

$R_{16}$ is a hydrogen atom or methyl group;

.... is a single or double bond;

~ indicates that the attached atom or group can be in either the $\alpha$ or $\beta$ configuration; and M is a lithium, sodium, potassium, magnesium or calcium atom.

2. A 17$\beta$-cyano-17$\alpha$-hydroxy steroid according to claim 1 where $R_9$ is nothing, $R_{11}$ is a hydrogen atom and the C-ring contains a $\Delta^{9(11)}$ double bond.

3. A 17-protected-17$\beta$-cyano-17$\alpha$-hydroxy steroid of the formula

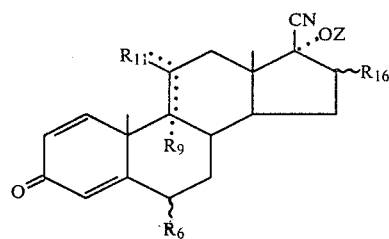
(II B)

and its $C_3$ protected enolate

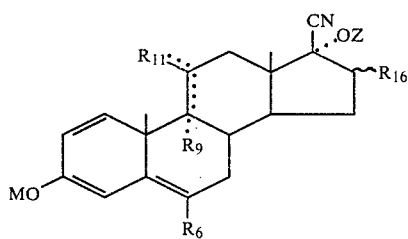
(IIBa)

where
$R_6$ is a hydrogen or fluorine atom, methyl or methylene group;
$R_9$ is nothing, a hydrogen, fluorine or oxygen atom, which makes the C ring
 (a) $\Delta^{9(11)}$ when $R_9$ is nothing and
 (b) $9\beta,11\beta$-epoxide when $R_9$ is an oxygen atom;
$R_{11}$ is a hydrogen or oxygen atom, two hydrogen atoms, or $\alpha$- or $\beta$-hydroxyl group which makes the C-ring
 (a) $\Delta^{9(11)}$ when $R_{11}$ is a hydrogen atom,
 (b) $9\beta,11\beta$-epoxide when $R_{11}$ is an oxygen atom and .... between $C_{11}$ and $R_{11}$ is a single bond, and
 (c) a ketone when $R_{11}$ is an oxygen atom and ... between $C_{11}$ and $R_{11}$ is a double bond;
$R_{16}$ is a hydrogen atom or methyl group;
Z is selected from the group consisting of a TMS, THP, methoxymethyl, t-butyldimethyl silyl and EEE group;
.... is a single or double bond;

~ indicates that the attached atom or group can be in either the $\alpha$ or $\beta$ configuration; and M is a lithium, sodium, potassium, magnesium or calcium atom.

4. A steroid selected from the group consisting of an enimide of the formula

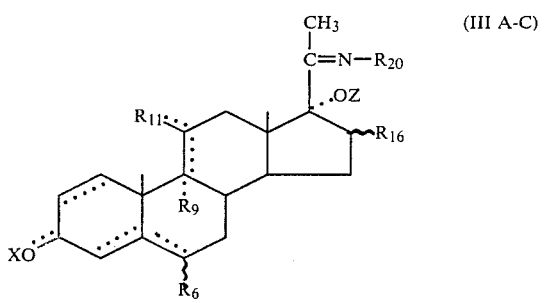
(III A-C)

and its $C_3$ protected forms

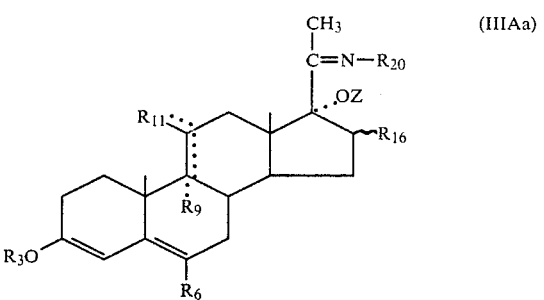
(IIIAa)

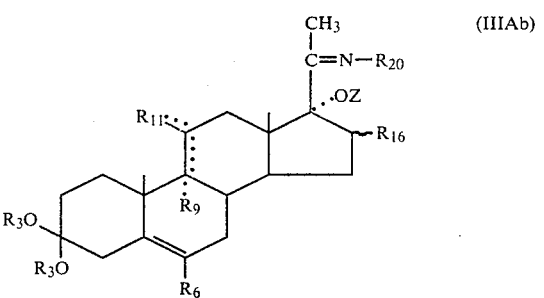
(IIIAb)

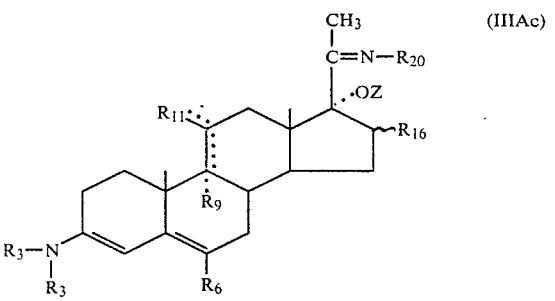
(IIIAc)

-continued

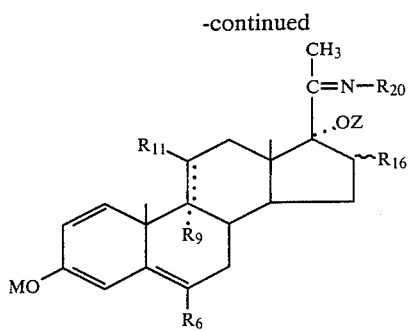 (IIIBa)

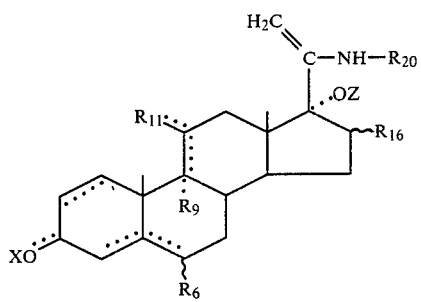 (IIICa)

or
an Δ²⁰-enamide of the formula

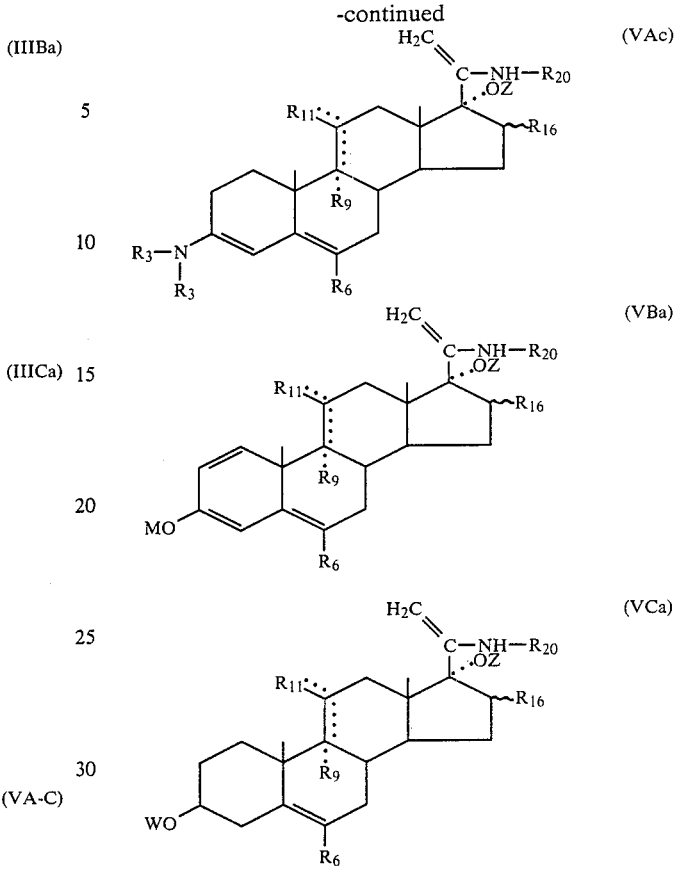

and its C₃ protected forms

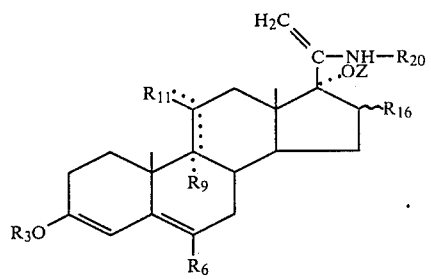 (VAa)

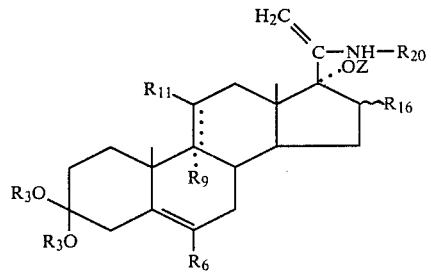 (VAb)

where
$R_6$ is a hydrogen or fluorine atom or methyl group;
$R_9$ is nothing, a hydrogen, fluorine or oxygen atom, which makes the C-ring
  (a) $\Delta^{9(11)}$ when $R_9$ is nothing and
  (b) 9β-,11β-epoxide when $R_9$ is an oxygen atom;
$R_{11}$ is a hydrogen or oxygen atom, two hydrogen atoms, or α- or β-hydroxyl group which makes the C-ring
  (a) $\Delta^{9(11)}$ when $R_{11}$ is a hydrogen atom,
  (b) 9β,11β-epoxide when $R_{11}$ is an oxygen atom and .... between $C_{11}$ and $R_{11}$ is a single bond, and
  (c) a ketone when $R_{11}$ is an oxygen atom and .... between $C_{11}$ and $R_{11}$ is a double bond;
$R_{16}$ is a hydrogen atom or methyl group;
$R_{20}$ is —OC—$R_{20}'$ or —$R_{20}''$;
$R_{20}'$ is alkyl of 1 thru 5 carbon atoms, phenyl, phenyl substituted 0 thru 2 chlorine atoms, methyl or nitro groups;
$R_{20}''$ is —Si(CH₃)₃ or Si(CH₃)₂C(CH₃)₃;
X refers to a hydrogen atom or nothing;
Z is selected from the group consisting of a TMS, THP, methoxymethyl, t-butyldimethyl silyl and EEE group;
.... is a single or double bond;
~ indicates that the attached atom or group can be in either the α or β configuration;
$R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

5. An enimide according to claim 4 where Z is selected from the group consisting of EEE, THP, TMS, and MEM.

6. An enimide according to claim 4 where $R_{20}$ is selected from the group consisting of acetyl, propionyl, benzoyl, formyl, trichloroacetyl, and trifluoroacetyl.

7. A process for the preparation of a $C_3$ protected enimide of the formula

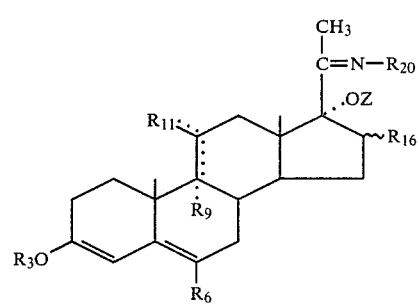
(IIIAa)

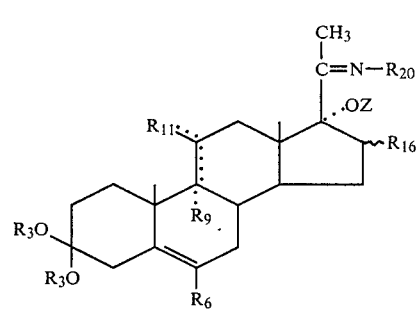
(IIIAb)

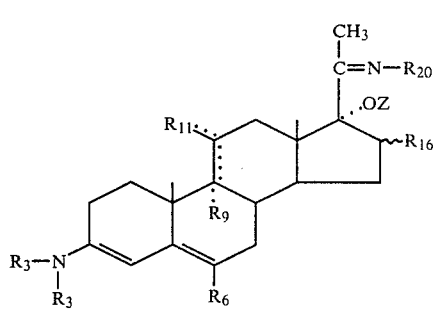
(IIIAc)

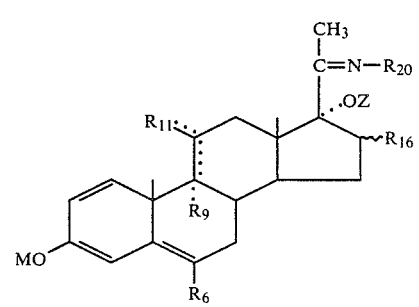
(IIIBa)

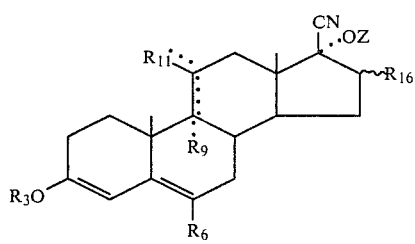
(IIICa)

which comprises (1) contacting a $C_3$ protected 17-protected-17β-cyano-17α-hydroxy steroid of the formula

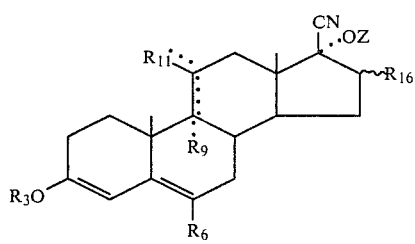
(II Aa)

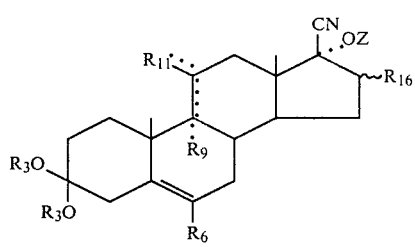
(II Ab)

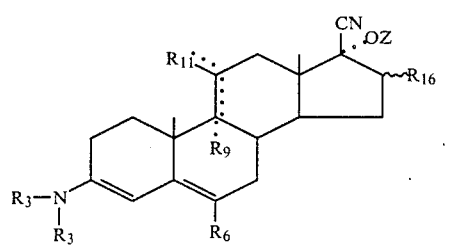
(II Ac)

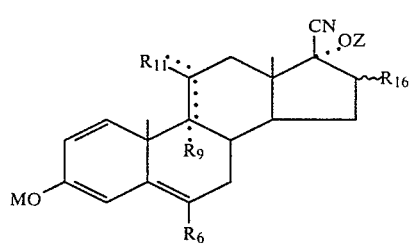
(II Ba)

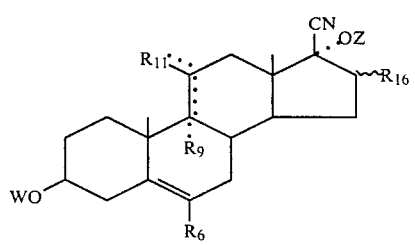
(II Ca)

with a methylating agent and (2) contacting the reaction mixture of step (1) with an acylating or silating agent where $R_6$ is a hydrogen or fluorine atom, methyl or methylene group;

$R_9$ is nothing, a hydrogen, fluorine or oxygen atom, which makes the C-ring
  (a) $\Delta^{9(11)}$ when $R_9$ is nothing and
  (b) $9\beta,11\beta$-epoxide when $R_9$ is an oxygen atom;

$R_{11}$ is a hydrogen or oxygen atom, two hydrogen atoms, or $\alpha$- or $\beta$-hydroxyl group which makes the C-ring
  (a) $\Delta^{9(11)}$ when $R_{11}$ is a hydrogen atom,
  (b) $9\beta,11\beta$-epoxide when $R_{11}$ is an oxygen atom and .... between $C_{11}$ and $R_{11}$ is a single bond, and
  (c) a ketone when $R_{11}$ is an oxygen atom and .... between $C_{11}$ and $R_{11}$ is a double bond;

$R_{16}$ is a hydrogen atom or methyl group;

$R_{20}$ is $-OC-R_{20}'$ or $-R_{20}''$;

$R_{20}'$ is alkyl of 1 thru 5 carbon atoms, phenyl, phenyl substituted 0 thru 2 chlorine atoms, methyl or nitro groups;

$R_{20}''$ is $-Si(CH_3)_3$ or $Si(CH_3)_2C(CH_3)_3$;

Z is selected from the group consisting of a TMS, THP, methoxymethyl, t-butyldimethyl silyl and EEE group;

.... is a single or double bond;

$\sim$ indicates that the attached atom or group can be in either the $\alpha$ or $\beta$ configuration;

$R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

8. A process according to claim 7 where the methylating agent is selected from the group consisting of methyl lithium, methyl magnesium bromide, methyl magnesium chloride and methyl magnesium iodide.

9. A process according to claim 7 where the acylating or silating agent is selected from the group consisting of $(R_{20})_2O$, $R_{20}J$, or $R_{20}''J$ and J is a chlorine, bromine or iodine atom.

10. A process according to claim 9 where the acylating agent is acetic anhydride or acetyl chloride.

11. A process for the preparation of a $C_3$ protected $\Delta^{20}$-enamide acylate of the formula

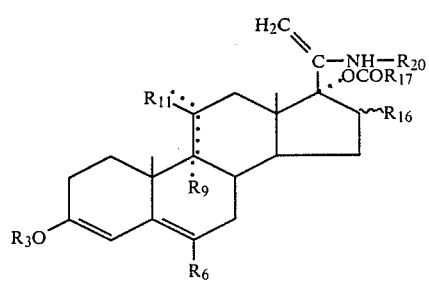
(IV Aa)

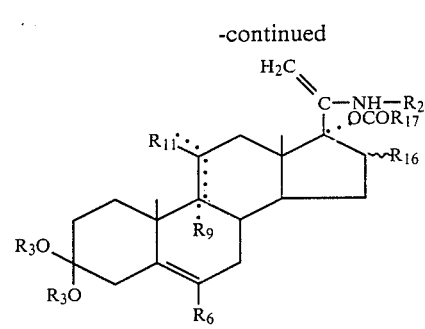
(IV Ab)

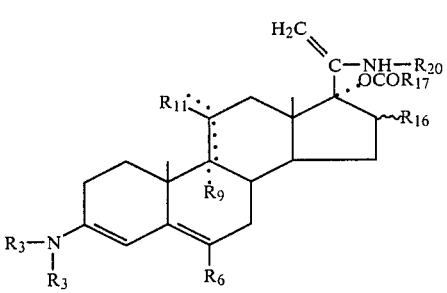
(IV Ac)

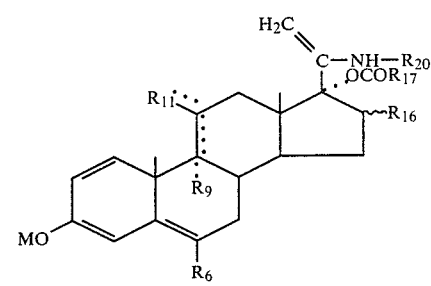
(IV Ba)

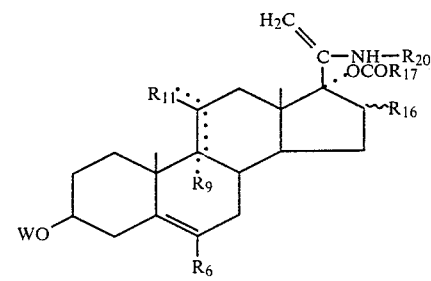
(IV Ca)

which comprises contacting a steroid selected from the group consisting of a $C_3$ protected enimide of the formula

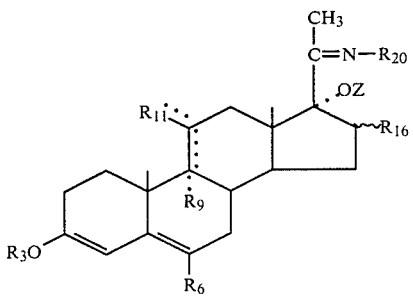
(IIIAa)

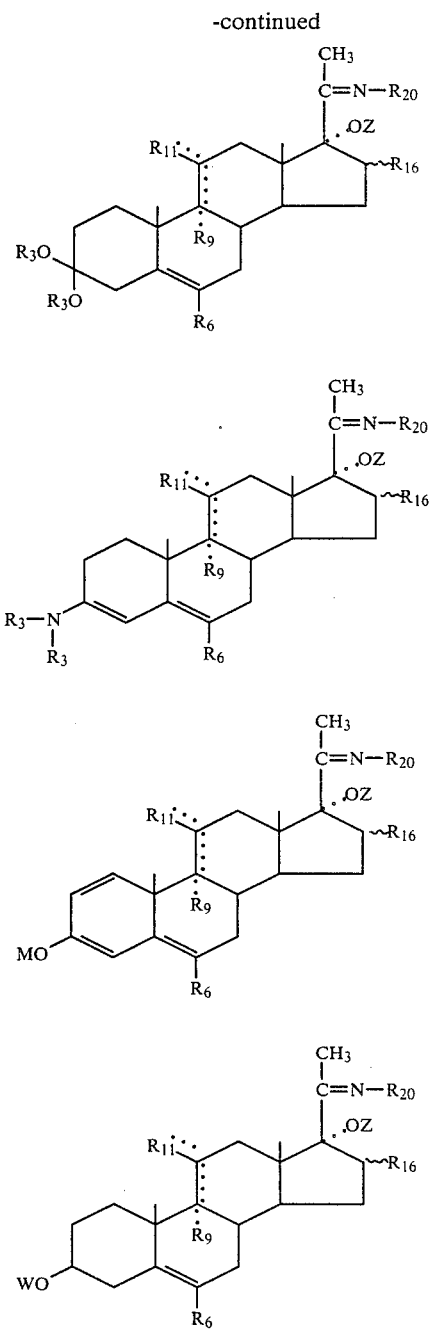

of a $C_3$ protected $\Delta^{20}$-enamide of the formula

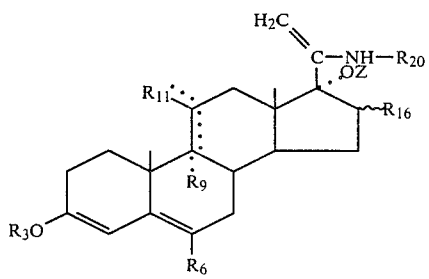

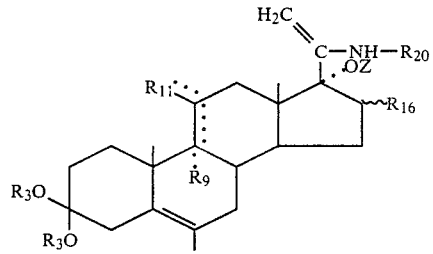

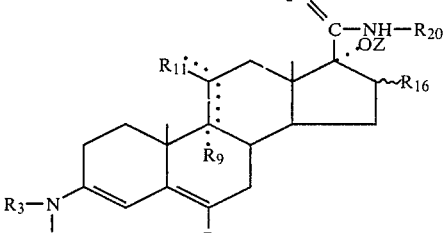

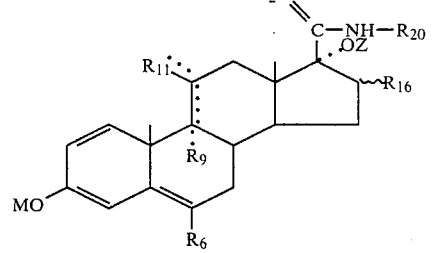

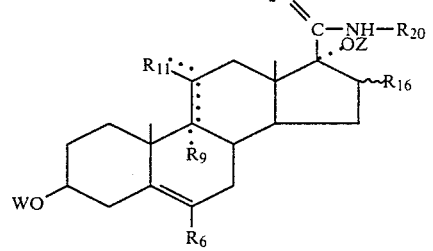

with a carboxylic acid of the formula $R_{17}COOH$ and an anhydride of the formula $(R_{17}CO)_2O$ where $R_6$ is a hydrogen or fluorine atom, methyl or methylene group;

$R_9$ is nothing, a hydrogen, fluorine or oxygen atom, which makes the C-ring
  (a) $\Delta^{9(11)}$ when $R_9$ is nothing and
  (b) $9\beta,11\beta$-epoxide when $R_9$ is an oxygen atom;

$R_{11}$ is a hydrogen or oxygen atom, two hydrogen atoms, or $\alpha$- or $\beta$-hydroxyl group which makes the C-ring
  (a) $\Delta^{9(11)}$ when $R_{11}$ is a hydrogen atom,
  (b) $9\beta,11\beta$-epoxide when $R_{11}$ is an oxygen atom and .... between $C_{11}$ and $R_{11}$ is a single bond, and
  (c) a ketone when $R_{11}$ is an oxygen atom and .... between $C_{11}$ and $R_{11}$ is a double bond;

$R_{16}$ is a hydrogen atom or methyl group;

$R_{17}$ is a hydrogen atom alkyl of 1 thru 5 carbon atoms, phenyl substituted with zero thru 2 chlorine atoms, trichloromethyl or trifluoromethyl groups;

$R_{20}$ is $-OC-R_{20}'$ or $-R_{20}''$;

$R_{20}'$ is alkyl of 1 thru 5 carbon atoms, phenyl, phenyl substituted 0 thru 2 chlorine atoms, methyl or nitro groups;

$R_{20}''$ is —Si(CH$_3$)$_3$ or Si(CH$_3$)$_2$C(CH$_3$)$_3$;

Z is selected from the group consisting of a TMS, THP, methoxymethyl, t-butyldimethyl silyl and EEE group;

. . . . is a single or double bond;

~ indicates that the attached atom or group can be in either the α or β configuration;

$R_3$ is alkyl of 1 thru 5 carbon atoms with the proviso that for the ketal (Ab) and the enamine (Ac), the $R_3$ groups can be connected and when connected may be connected by an oxygen or nitrogen atom;

M is a lithium, sodium, potassium, magnesium or calcium atom; and

W is a TMS, THP, or ethoxy ethyl group.

12. A process according to claim 11 where $R_{17}$ is methyl, ethyl or phenyl.

13. A process for the preparation of a C$_3$ protected Δ$^{20}$-enamide of the formula

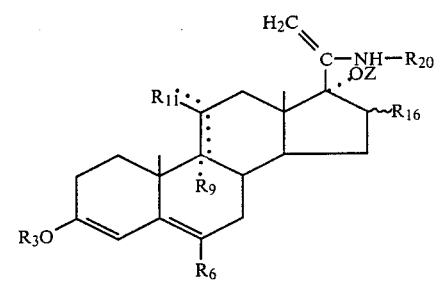
(VAa)

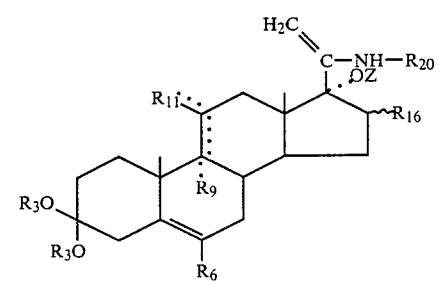
(VAb)

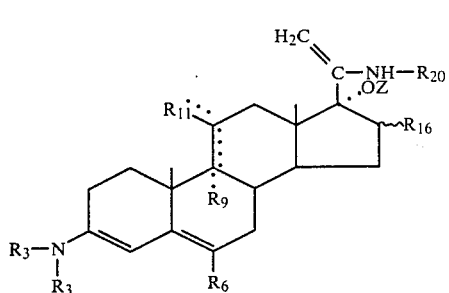
(VAc)

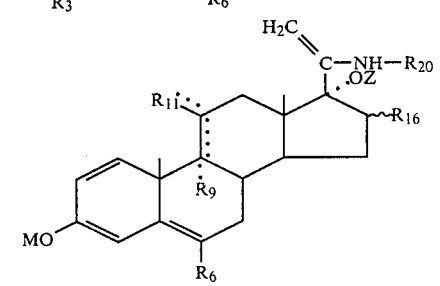
(VBa)

which comprises contacting a C$_3$-protected enimide of the formula

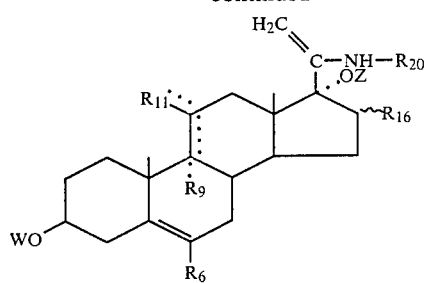
(VCa)

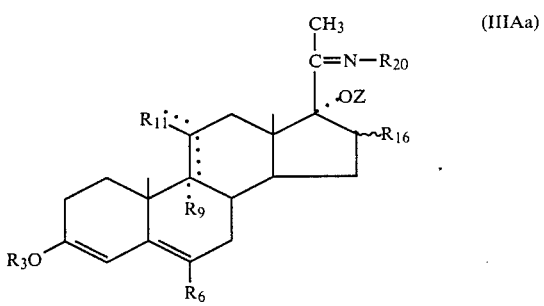
(IIIAa)

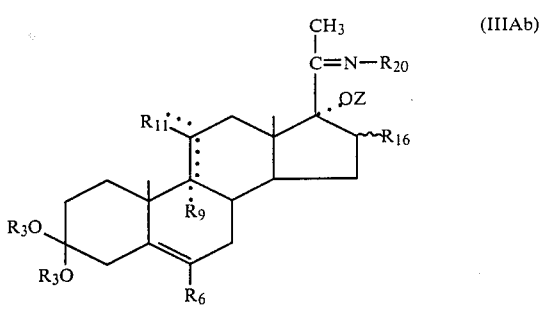
(IIIAb)

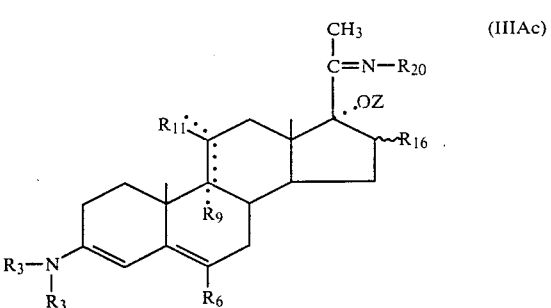
(IIIAc)

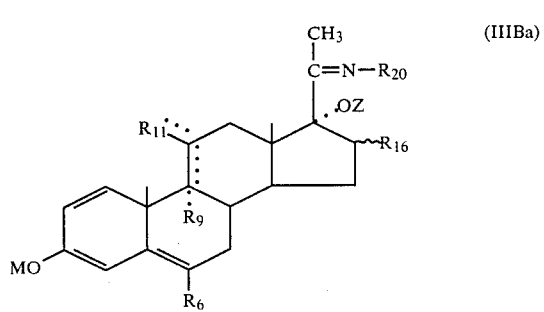
(IIIBa)

-continued

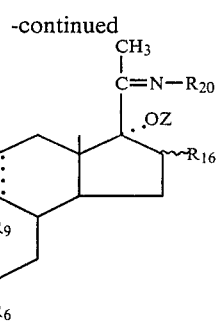
(IIICa)

with an acid or base where
$R_6$ is a hydrogen or fluorine atom, methyl or methylene group;
$R_9$ is nothing, a hydrogen, fluorine or oxygen atom, which makes the C-ring
(a) $\Delta^{9(11)}$ when $R_9$ is nothing and
(b) $9\beta,11\beta$-epoxide when $R_9$ is an oxygen atom;
$R_{11}$ is a hydrogen or oxygen atom, two hydrogen atoms, or $\alpha$- or $\beta$-hydroxyl group which makes the C-ring
(a) $\Delta^{9(11)}$ when $R_{11}$ is a hydrogen atom,
(b) $9\beta,11\beta$-epoxide when $R_{11}$ is an oxygen atom and .... between $C_{11}$ and $R_{11}$ is a single bond, and
(c) a ketone when $R_{11}$ is an oxygen atom and .... between $C_{11}$ and $R_{11}$ is a double bond;
$R_{16}$ is a hydrogen atom or methyl group;
$R_{20}$ is $-OC-R_{20}'$ or $-R_{20}''$;
$R_{20}'$ is alkyl of 1 thru 5 carbon atoms, phenyl, phenyl substituted 0 thru 2 chlorine atoms, methyl or nitro groups;
$R_{20}''$ is $-Si(CH_3)_3$ or $Si(CH_3)_2C(CH_3)_3$;
Z is selected from the group consisting of a TMS, THP, methoxymethyl, t-butyldimethyl silyl and EEE group;
.... is a single or double bond;
~ indicates that the attached atom or group can be in either the $\alpha$ or $\beta$ configuration;
$R_3$ is alkyl of 1 thru 5 carbon atoms with the proviso that for the ketal (Ab) and the enamine (Ac), the $R_3$ groups can be connected and when connected may be connected by an oxygen or nitrogen atom;
M is a lithium, sodium, potassium, magnesium or calcium atom; and
W is a TMS, THP, or ethoxy ethyl group.

14. A process according to claim 13 where the acid is a Lewis acid or carboxylic acid.

15. A process according to claim 14 where the acid is selected from the group consisting of acetic, propionic, benzoic or citric acid.

16. A process according to claim 13 where the base is selected from the group consisting of DBU, DBN, amidine bases of the formula

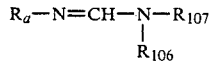

and guanidine bases of the formula

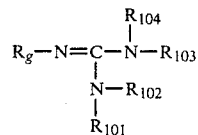

where
$R_a$ is alkyl of 1 thru 7 carbon atoms, cycloalkyl of 5 thru 7 carbon atoms, phenyl substituted with 1 thru 3 $-R_{100}$, $-OR_{105}$ or $-N(R_{105})_2$ where with the amine the $R_{105}$'s can be the same or different and can be combined to form a cyclic secondary amine selected from the group consisting of piperidine, pyrrolidine and morpholine;
$R_g$ is $R_a$, a hydrogen atom or phenyl;
$R_{101}$ is alkyl of 1 thru 7 carbon atoms, cycloalkyl of 5 thru 7 carbon atoms, phenyl substituted with 1 thru 3 $-R_{100}$, $-OR_{105}$ or $-N(R_{105})_2$ where with the amine the $R_{105}$'s can be the same or different and can be combined to form a cyclic secondary amine selected from the group consisting of piperidine, pyrrolidine and morpholine;
$R_{102}$ is alkyl of 1 thru 7 carbon atoms, cycloalkyl of 5 thru 7 carbon atoms, phenyl substituted with 1 thru 3 $-R_{100}$, $-OR_{105}$ or $-N(R_{105})_2$ where with the amine the $R_{105}$'s can be the same or different and can be combined to form a cyclic secondary amine selected from the group consisting of piperidine, pyrrolidine and morpholine;
$R_{103}$ is alkyl of 1 thru 7 carbon atoms, cycloalkyl of 5 thru 7 carbon atoms, phenyl substituted with 1 thru 3 $-R_{100}$, $-OR_{105}$ or $-N(R_{105})_2$ where with the amine the $R_{105}$'s can be the same or different and can be combined to form a cyclic secondary amine selected from the group consisting of piperidine, pyrrolidine and morpholine;
$R_{104}$ is alkyl of 1 thru 7 carbon atoms, cycloalkyl of 5 thru 7 carbon atoms, phenyl substituted with 1 thru 3 $-R_{100}$, $-OR_{105}$ or $-N(R_{105})_2$ where with the amine the $R_{105}$'s can be the same or different and can be combined to form a cyclic secondary amine selected from the group consisting of piperidine, pyrrolidine and morpholine;
$R_{106}$ is alkyl of 1 thru 7 carbon atoms, cycloalkyl of 5 thru 7 carbon atoms, phenyl substituted with 1 thru 3 $-R_{100}$, $-OR_{105}$ or $-N(R_{105})_2$ where with the amine the $R_{105}$'s can be the same or different and can be combined to form a secondary amine selected from the group consisting of piperidine, pyrrolidine or morpholine with the proviso that $R_{106}$ and $R_{107}$ combined cannot have more than 14 carbon atoms; $R_{106}$ and $R_{107}$ can be combined to form a secondary cyclic amine selected from the group consisting of piperidine, pyrrolidine and morpholine;
$R_{107}$ is alkyl of 1 thru 7 carbon atoms, cycloalkyl of 5 thru 7 carbon atoms, phenyl substituted with 1 thru 3 $-R_{100}$, $-OR_{105}$ or $-N(R_{105})_2$ where with the amine the $R_{105}$'s can be the same or different and can be combined to form a secondary amine selected from the group consisting of piperidine, pyrrolidine or morpholine with the proviso that $R_{106}$ and $R_{107}$ combined cannot have more than 14 carbon atoms; $R_{106}$ and $R_{107}$ can be combined to form a secondary cyclic amine selected from the group consisting of piperidine, pyrrolidine and morpholine.

17. A 17$\beta$-cyano-17$\alpha$-hydroxy steroid according to claim 1 which is selected from the group consisting of 17$\beta$-cyano-11$\beta$,17$\alpha$-dihydroxyandrosta-1,4-dien-3-one and 17$\beta$-cyano-11$\beta$,17$\alpha$-dihydroxy-6$\alpha$-methylandrosta-1,4-dien-3-one.

18. An enimide according to claim 4 which is selected from the group consisting of a 17$\alpha$-($\alpha$-ethoxyethyl)-ether-20-acetylaminopregn-5-en-3-ethylidine ketal, and 17$\alpha$-($\alpha$-ethoxyethyl)-ether-20-trifluoroacetylaminopregn-5-ene-3-ethylidine ketal.

* * * * *

UNITED STATES PATENT OFFICE
CERTIFICATE OF CORRECTION

Patent No. 4,548,748    Dated October 22, 1985

Inventor(s) Verlan H. VanRheenen

It is certified that error appears in the above-identified patent and that said Letters Patent are hereby corrected as shown below:

Column 3, line 14, "(II A-C)" should read --(III A-C)--
Column 3, line 63, "will" should read --well--
Column 9, line 23, "..." should read --....--
Column 9, line 25, "...." should read --....--
Column 10, line 13, "thru 2" should read --thru 3--
Column 10, line 37, "...." should read --....--
Column 17, line 67, "(0.125 )" should read --(0.125 ml)--
Column 18, line 48, "5-3-ethylidine" should read --5-en-3-ethylidine--
Column 19, line 53, "$\lfloor OCOR_{17}$" should read --$\lfloor .OCOR_{17}$--

Column 21, line 31, "  " should read --

Column 21, line 41, " 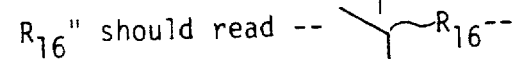 " should read --

Column 21, line 53, " 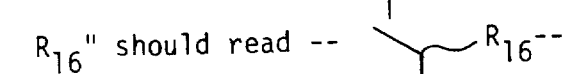 " should read --

Column 21, line 65, " 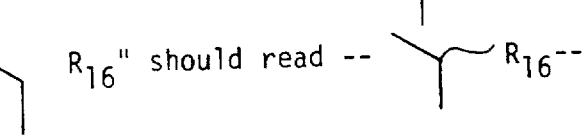 " should read --

Column 23, lines 6 & 7, "  " should read --

Column 25, line 23, ".... between" should read --.... between--
Column 25, line 25, "and ...." should read --and ....--
Column 25, line 28, ".... is a" should read --.... is a--
Column 25, line 65, ".... between" should read --.... between--
Column 25, line 66, "and ...." should read --and ....--
Column 26, line 4, ".... is a" should read --.... is a--
Column 26, line 50, ".... between" should read --.... between--
Column 26, line 51, "and ...." should read --and ....--

UNITED STATES PATENT OFFICE
CERTIFICATE OF CORRECTION

Patent No. 4,548,748　　　　　　　　Dated October 22, 1985

Inventor(s) Verlan H. VanRheenen

It is certified that error appears in the above-identified patent and that said Letters Patent are hereby corrected as shown below:

Column 26, line 64, ".... is a" should read --.... is a--
Column 28, line 49, ".... between" should read --.... between--
Column 28, line 50, "and ...." should read --and ....--
Column 28, line 64, ".... is a" should read --.... is a--
Column 29, lines 11-13, (Ab) "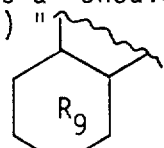" should read --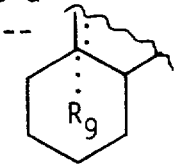--

Column 29, line 23 (Ac) "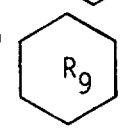" should read --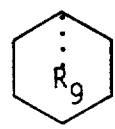--

Column 30, line 11, "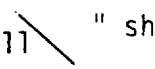" should read ----

Column 30, line 65, ".... between" should read --.... between--
Column 30, line 66, "and ...." should read --and ....--
Column 31, line 13, ".... is a" should read --.... is a--
Column 31, lines 49-50, "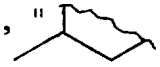" should read --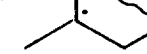--

Column 31, lines 61-62, "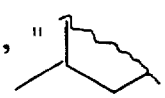" should read ----

Column 32, line 53, ".... between" should read --.... between--
Column 32, line 54, "and ...." should read --and ....--
Column 32, line 66, ".... is a" should read --.... is a--
Column 33, line 28, "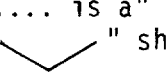" should read ----

UNITED STATES PATENT OFFICE
CERTIFICATE OF CORRECTION

Patent No. 4,548,748   Dated October 22, 1985

Inventor(s) Verlan H. VanRheenen

It is certified that error appears in the above-identified patent and that said Letters Patent are hereby corrected as shown below:

Column 35, line 49, ".... between" should read --.... between--
Column 35, line 50, "and ...." should read --and ....--
Column 35, line 63, ".... is a" should read --.... is a--
Column 37, line 38, " 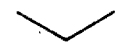 " should read --  --

Column 37, line 68, ".... between" should read --.... between--
Column 38, line 1, "and ...." should read --and ....--
Column 38, line 20, ".... is a" should read --.... is a--
Column 39, line 64, " 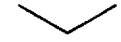 " should read --  --

Column 40, line 28, ".... between" should read --.... between--
Column 40, line 29, "and ...." should read --and ....--
Column 40, line 43, ".... is a" should read --.... is a--
Column 42, line 32, "$R9$" should read --$R_9$--

Column 42, line 41, ".... between" should read --.... between--
Column 42, line 42, "and ...." should read --and ....--
Column 42, line 55, ".... is a" should read --.... is a--
Column 44, line 28, ".... between" should read --.... between--
Column 44, line 29, "and ...." should read --and ....--
Column 44, line 42, ".... is a" should read --.... is a--
Column 45, line 68, ".... between" should read --.... between--
Column 46, line 1, "and ...." should read --and ....--
Column 46, line 4, ".... is a" should read --.... is a--
Column 46, lines 35-36, "11β,(α-" should read --11β,17α- --
Column 46, line 37, "6-methylandrost" should read --6α-methylandrost--

UNITED STATES PATENT OFFICE
CERTIFICATE OF CORRECTION

Patent No. 4,548,748                    Dated October 22, 1985

Inventor(s) Verlan H. VanRheenen

It is certified that error appears in the above-identified patent and that said Letters Patent are hereby corrected as shown below:

Column 49, line 6, (IIIBa), " $R_{11}$╲ " should read -- $R_{11}$╲⋰ --

Column 49, line 18, (IIICa), " $R_{11}$╲ " should read -- $R_{11}$╲⋰ --

Column 49, line 60, (VAb), " $R_{11}$╲ " should read -- $R_{11}$╲⋰ --

Signed and Sealed this

Eighteenth Day of November, 1986

Attest:

DONALD J. QUIGG

Attesting Officer          Commissioner of Patents and Trademarks